US006228085B1

(12) United States Patent
Theken et al.

(10) Patent No.: US 6,228,085 B1
(45) Date of Patent: May 8, 2001

(54) BONE FIXATION SYSTEM

(75) Inventors: Randall R. Theken, Barberton; Lukas Eisermann, Cleveland, both of OH (US); Ben Taylor, Hertfordshire (GB)

(73) Assignee: Theken Surgical LLC, Barberton, OH (US)

( * ) Notice: Subject to any disclaimer, the term of this patent is extended or adjusted under 35 U.S.C. 154(b) by 0 days.

(21) Appl. No.: 09/114,996

(22) Filed: Jul. 14, 1998

(51) Int. Cl.[7] .................................................. A61B 17/56
(52) U.S. Cl. ................................................................ 606/61
(58) Field of Search .............................. 606/61, 64, 69, 606/70, 71, 60; 623/17, 17.11, 17.16

(56) References Cited

U.S. PATENT DOCUMENTS

| | | |
|---|---|---|
| 1,105,105 | 7/1914 | Sherman . |
| 4,401,112 * | 8/1983 | Rezaian .................................. 606/61 |
| 4,445,513 | 5/1984 | Ulrich et al. . |
| 4,599,086 * | 7/1986 | Doty ....................................... 606/61 |
| 4,743,256 | 5/1988 | Brantigan . |
| 4,820,305 | 4/1989 | Harms et al. . |
| 4,892,545 * | 1/1990 | Day et al. .............................. 606/61 |
| 5,085,660 | 2/1992 | Lin . |
| 5,108,395 | 4/1992 | Laurain . |
| 5,147,361 | 9/1992 | Ojima et al. . |
| 5,151,103 | 9/1992 | Tepic et al. . |
| 5,176,680 * | 1/1993 | Vignaud et al. ....................... 606/60 |
| 5,192,327 | 3/1993 | Brantigan . |
| 5,261,910 | 11/1993 | Warden et al. . |
| 5,324,290 | 6/1994 | Zdeblick et al. . |
| 5,344,421 * | 9/1994 | Crook .................................... 606/70 |
| 5,360,431 | 11/1994 | Puno et al. . |
| 5,395,372 | 3/1995 | Holt et al. . |
| 5,405,391 * | 4/1995 | Hednerson et al. ................... 606/61 |
| 5,423,826 | 6/1995 | Coates et al. . |

(List continued on next page.)

FOREIGN PATENT DOCUMENTS

| | | |
|---|---|---|
| 1046827 | 10/1955 | (DE) . |
| 2933637 A1 | 4/1980 | (DE) . |
| 3442004 C1 | 4/1986 | (DE) . |
| 0 179 695 | 9/1984 | (EP) . |
| 179695 * | 4/1986 | (EP) ..................................... 623/17 |
| 0196206 A2 | 10/1986 | (EP) . |

(List continued on next page.)

OTHER PUBLICATIONS

"University[AM] Plate Titanium Anterior System", by Howard S. An, M.D., and Robert A. McGuire, M.D., AcroMed, pp. 1–8, 1996.
"Kaneda SR™ Anterior Spinal System", by Kiyoshi Kaneda, M.D., and Robert W. Gaines, Jr., M.D., AcroMed, pp. 1–11.

(List continued on next page.)

Primary Examiner—Gene Mancene
Assistant Examiner—Eduardo C. Robert
(74) Attorney, Agent, or Firm—Frost Brown Todd LLC; Robert H. Eichenberger

(57) ABSTRACT

An internal bone fixation system for the treatment of bone anomalies, such as thoraco-lumbar spinal instability. In accordance with a preferred embodiment, the fixation system includes a plate anatomically contoured to match the profile of lateral aspects common to thoracic and lumbar vertebrae, as well as the anterior profile. The contour of the plate allows for quicker implantation time, a lower profile, and a fit which allows for biomechanical load-sharing which increases the mechanical properties of the construct (i.e., stiffness, strength, and fatigue life). Moreover, the fixation system includes a fastener screw-plate interface which forces proper alignment between fastener screws and the plate, provides "pull-out" resistance and evenly distributes stresses on both the screw and the plate. Ledges are located on the medial surface at either end of the plate. The fixation system also includes set screws which effectively turn the screw construct into a bolt construct.

33 Claims, 21 Drawing Sheets

U.S. PATENT DOCUMENTS

| | | | |
|---|---|---|---|
| 5,458,641 | * 10/1995 | Ramirez Jimenez | 623/17 |
| 5,462,722 | * 10/1995 | Liu et al. | 423/311 |
| 5,466,237 | 11/1995 | Byrd, III et al. | |
| 5,474,555 | 12/1995 | Puno et al. | |
| 5,496,321 | 3/1996 | Puno et al. | |
| 5,520,690 | 5/1996 | Errico et al. | |
| 5,531,746 | 7/1996 | Errico et al. | |
| 5,534,031 | * 7/1996 | Matsuzaki et al. | 606/61 |
| 5,549,612 | 8/1996 | Yapp et al. | |
| 5,578,034 | 11/1996 | Estes. | |
| 5,601,553 | 2/1997 | Trebing et al. | |
| 5,603,714 | 2/1997 | Kaneda et al. | |
| 5,607,426 | 3/1997 | Ralph et al. | |
| 5,609,637 | 3/1997 | Biedermann et al. | |
| 5,616,144 | 4/1997 | Yapp et al. | |
| 5,624,442 | 4/1997 | Mellinger et al. | |
| 5,648,097 | * 7/1997 | Nuwayser | 424/489 |
| 5,676,666 | 10/1997 | Oxland et al. | |
| 5,681,310 | * 10/1997 | Yuan et al. | 606/61 |
| 5,681,312 | 10/1997 | Yuan et al. | |
| 5,697,929 | 12/1997 | Mellinger. | |
| 5,713,900 | 2/1998 | Benzel et al. | |
| 5,800,433 | * 9/1998 | Benzel et al. | 606/60 |
| 5,904,683 | * 5/1999 | Pohndorf et al. | 6306/61 |

FOREIGN PATENT DOCUMENTS

| | | |
|---|---|---|
| 1105392 | 7/1954 | (FR). |
| 2501033 | 9/1982 | (FR). |
| 2 726 755 | 11/1994 | (FR). |
| 2 747 034 | 4/1996 | (FR). |
| 1526673 | * 12/1989 | (SU) ........ 606/60 |
| 9417744 | * 8/1994 | (WO) ........ 606/61 |
| 9426193 | * 11/1994 | (WO) ........ 606/61 |

OTHER PUBLICATIONS

"Ligament Strain and Ankle Joint Opening During Ankle Distraction", by Randy Theken, M.S., et al., *Arthroscopy: The Journal of Arthroscopic and Related Surgery*, pp. 469–473, 1992.

"Basilar Crescentic Osteotomy A Three–Dimensional Computer Simulation", by Randy Theken, M.S., et al., *Orthopedic Clinics of North America*, vol. 20, No. 4, Oct. 1989, pp. 571–582.

"A Theoretical Finite Element and Biomechanical Analysis of Transpedicular Screws for Fixation of the Spine", by Randall Theken, M.S., et al., First presented at *The 2nd International Meeting on Advanced Spine Techniques*, Apr. 26–29, 1995.

"Fatigue Characterization of Anterior Screw/Rod Constructs in Axial Compression", by Randall R. Theken, M.S., et al., First presented at *The 2nd International Meeting on Advanced Spine Techniques*, Apr. 26–29, 1995.

"Fatigue Characterization of Hook/Rod Assemblies Loaded in Compression", by Randall R. Theken, M.S., et al., First presented at *The 2nd International Meeting on Advanced Spine Techniques*, Apr. 26–29, 1995.

Theken Orthopaedic Brochure, *Pinnacle*, 1994.

* cited by examiner

BONE FIXATION SYSTEM

FIELD OF INVENTION

The present invention relates generally to a bone fixation system, and more particularly to an internal bone fixation system for the treatment of bone anomalies, such as thoraco-lumbar spinal instability.

BACKGROUND OF THE INVENTION

Trauma, lumbar burst fractures, tumors, severe disc degeneration, and anterior fusion following multiple posterior operations, are just some of the causes of anterior thoraco-lumbar spinal instability. Anterior treatment of thoraco-lumbar spinal instability has included the use of a conventional fixation system comprised of a generally planar plate and fasteners. The plate is arranged between a pair of vertebrae, and has openings for receiving the fasteners. The fasteners engage the appropriate vertebra to affix the plate thereto.

Prior art fixation systems have several disadvantages. In this respect, the fixation systems have relatively flat plates that connect to the vertebrae by some combination of bolts or screws. Loading of such an implant system is primarily onto the smallest, weakest, and least stiff components of the fixation system. The entire load is taken by the screws at one end of the plate, and transferred through the plate to the screws at the other end of the plate. Furthermore, maximal stress on the plate occurs at the tensile (lateral) side of the plate. Accordingly, the stiffness, strength and fatigue properties of prior art fixation systems are deficient.

Moreover, prior art fixation systems have a profile that matches only the anterior profile of the vertebral bodies. As a result, surgeons are forced to cut a channel in the bone in order for the plate to fit properly. This leads to complex surgical procedures, long implantation times, and an anatomical fit which does not allow for biomechanical load-sharing which leads to improvements in mechanical properties such as stiffness, strength and fatigue life.

The present invention addresses these and other drawbacks of prior art bone fixation systems.

SUMMARY OF THE INVENTION

According to the present invention, there is provided a bone fixation system comprised of a plate and fasteners, wherein said plate is dimensioned to fit both the anterior and lateral profile of vertebral bodies.

An advantage of the present invention is the provision of a bone fixation system having greater stiffness than prior art systems.

Another advantage of the present invention is the provision of a bone fixation system having greater strength than prior art systems.

Still another advantage of the present invention is the provision of a bone fixation system having greater fatigue life than prior art systems.

Still another advantage of the present invention is the provision of a bone fixation system having an enhanced screw-plate interface for easier installation and improved security over prior art systems.

Still another advantage of the present invention is the provision of a bone fixation system having a plate contoured to fit the lateral profile of the vertebrae, thus providing added thickness for improved rigidity and forming a ledge for supporting the vertebrae in direct compression.

Yet another advantage of the present invention is the provision of a bone fixation system having an improved anatomical fit over prior art systems.

Yet another advantage of the present invention is the provision of a bone fixation system that provides improved interoperative graft access and postoperative graft evaluation.

Yet another advantage of the present invention is the provision of a bone fixation system requiring less surgical complexity for installation.

Yet another advantage of the present invention is the provision of a fastener system for securely fastening a plate to a bone structure.

Still other advantages of the invention will become apparent to those skilled in the art upon a reading and understanding of the following detailed description, accompanying drawings and appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENT

It should be appreciated that while a preferred embodiment of the present invention will be described with particular reference to a bone fixation system for anterior treatment of thoraco-lumbar spinal instability, the present invention is also contemplated for use in connection with the treatment of other bone anomalies. In this regard, the present invention finds application in the treatment of bone structures in other regions of the spine, as well as bones located in regions outside the spine.

Figure 1:
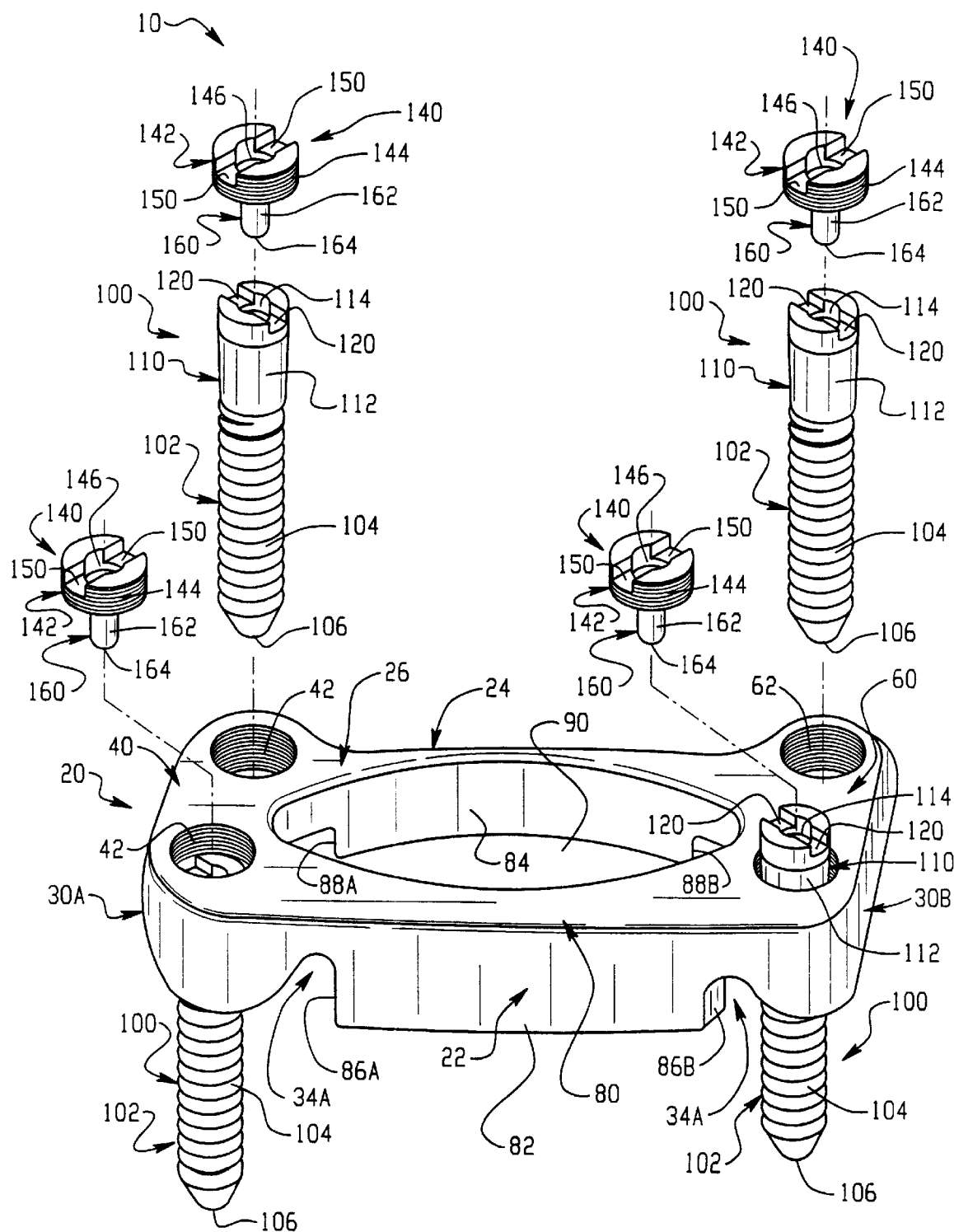
FIG. 1 is an exploded perspective view of the bone fixation system according to a preferred embodiment of the present invention.
Figure 2:
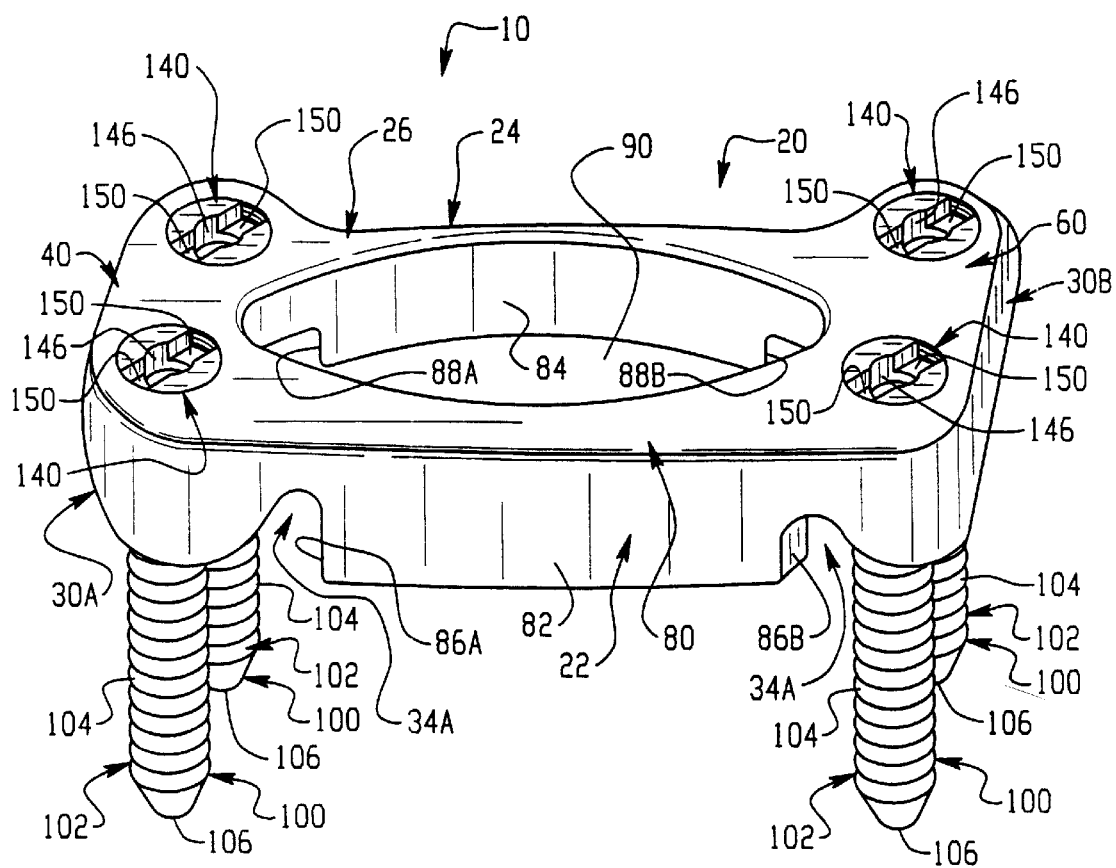
FIG. 2 is a perspective of the bone fixation system according to a preferred embodiment of the present invention.
Figure 3:
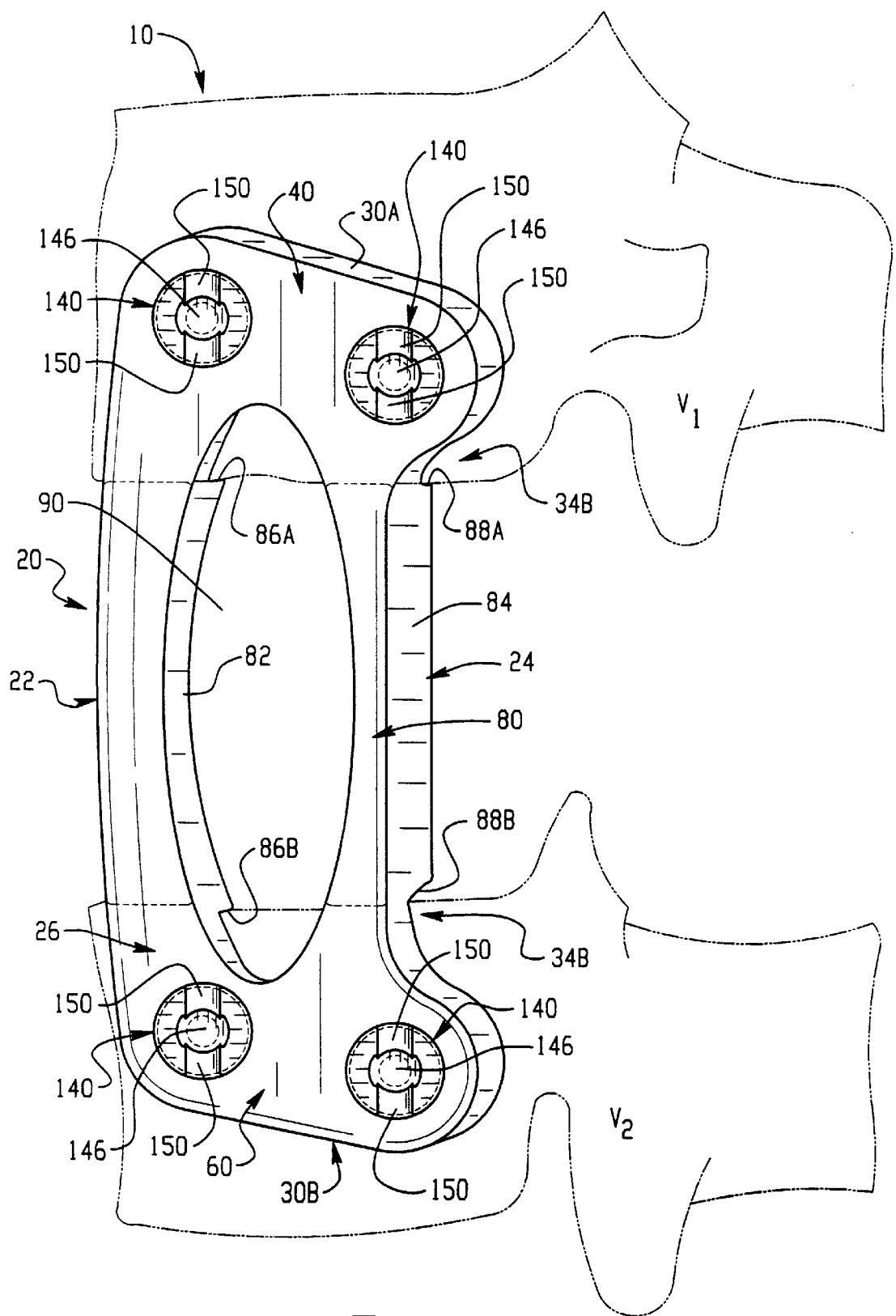
FIG. 3 is a lateral side view of the bone fixation system according to a preferred embodiment of the present invention, as affixed to a pair of vertebral bodies.
Figure 4:
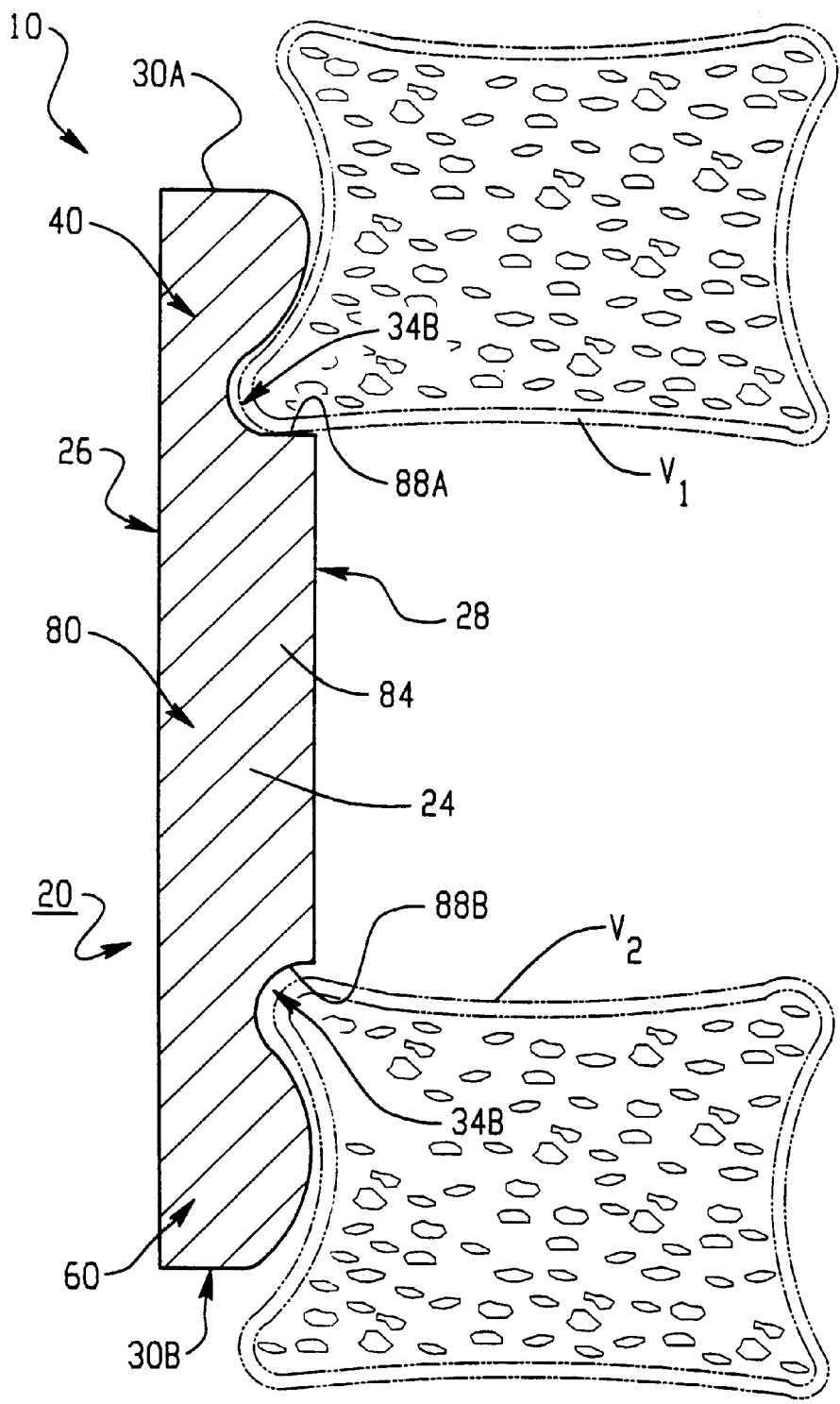
FIG. 4 is a posterior sectional view of the bone fixation system, as affixed to a pair of vertebral bodies.
Figure 5:
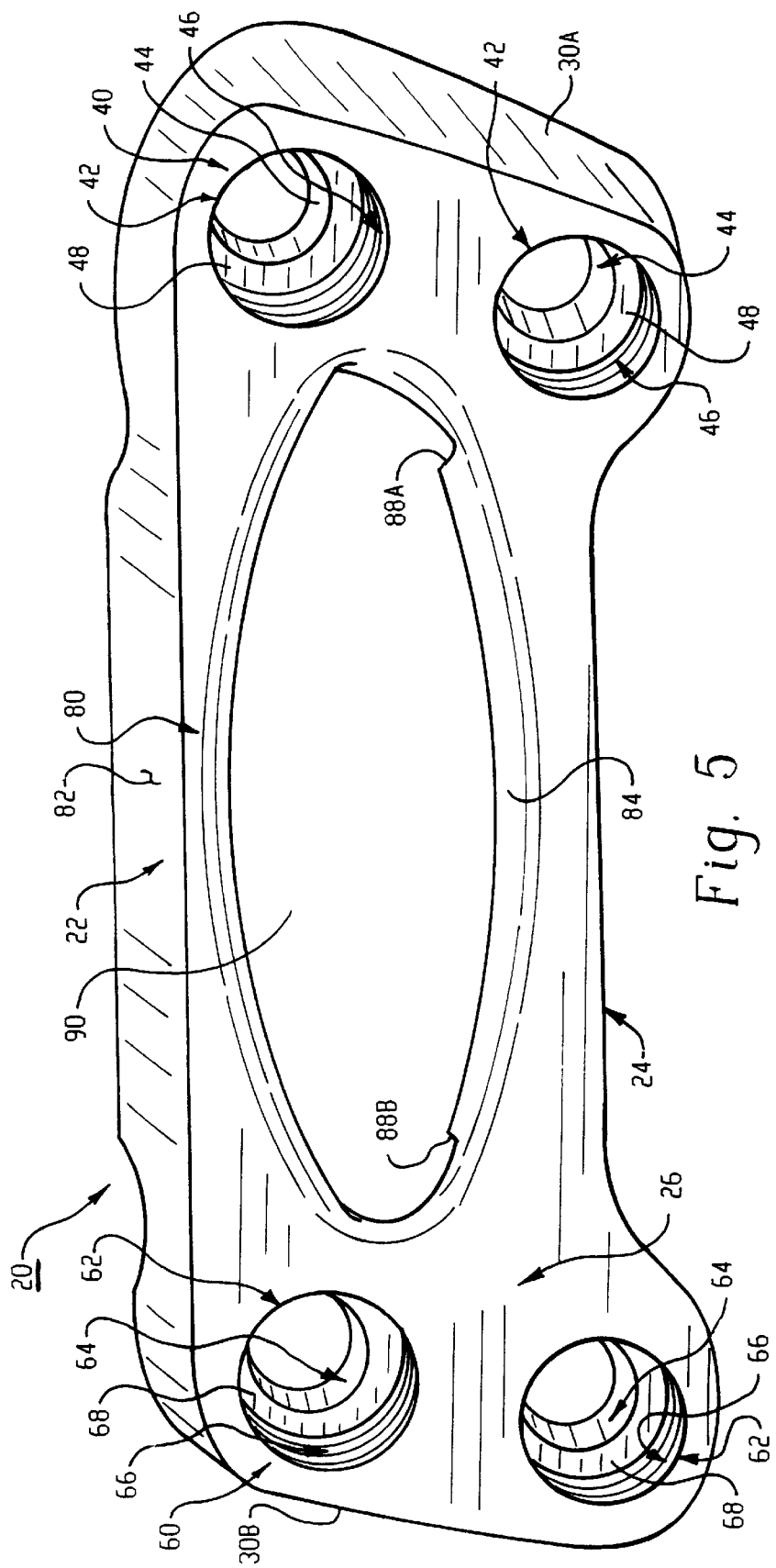
FIG. 5 is a lateral side view of the bone plate.
Figure 6:
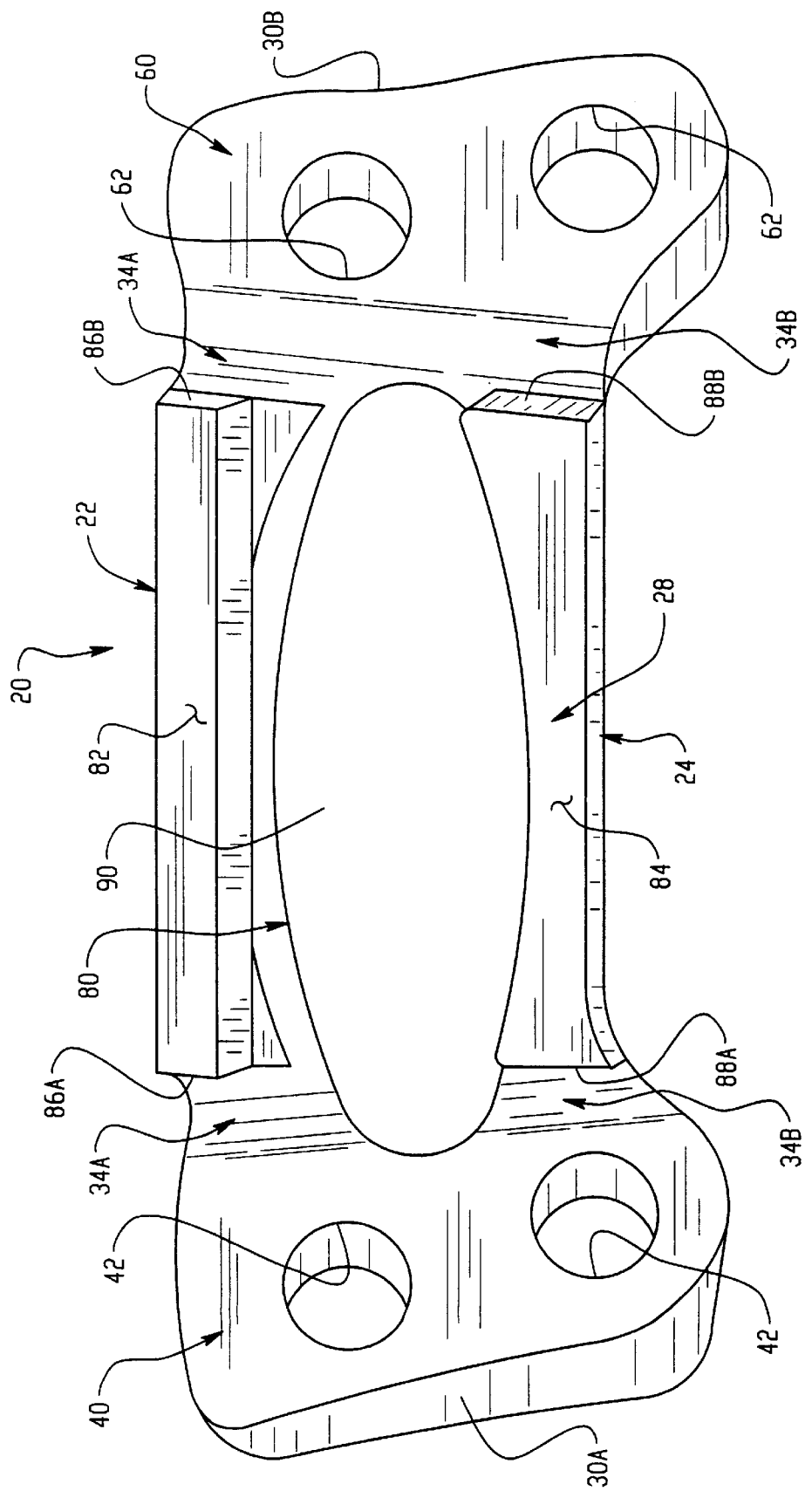
FIG. 6 is a medial side view of the bone plate shown in FIG. 5.
Figure 7:
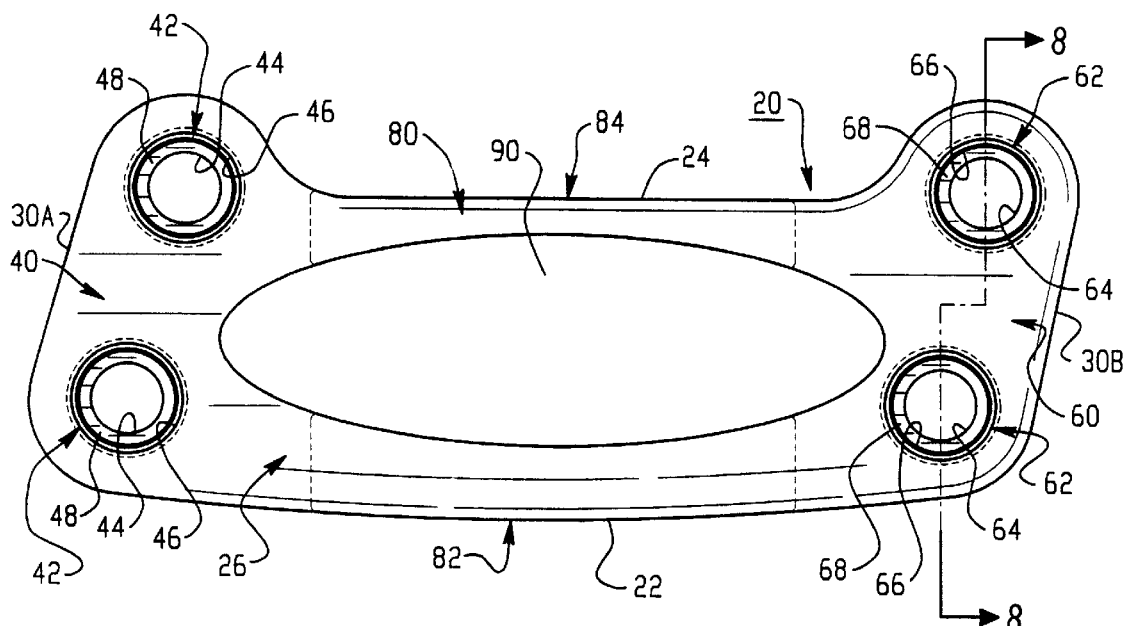
FIG. 7 is a top plan view of the lateral side of the bone plate.

Referring now to the drawings wherein the showings are for the purposes of illustrating a preferred embodiment of the invention only and not for purposes of limiting same, FIG. 1 shows an exploded view of a bone fixation system 10, according to a preferred embodiment of the present invention. Fixation system 10 is generally comprised of a bone plate 20, a plurality of bone screws 100, and a plurality of set screws 140. As fully assembled, screws 100 are inserted through holes formed in plate 20 and driven into a bone structure (e.g., a vertebral body). Set screws 140 are also arranged inside the holes to further lock screws 100 in position (FIG. 2). FIGS. 3 and 4 illustrate fixation system 10 as attached to vertebral bodies $V_1$ and $V_2$. A complete description of the assembly and installation of fixation system 10 is provided in detail below. In the preferred embodiment illustrated herein, fixation system 10 is configured for treatment of vertebrae T11 to L3.

Turning now to FIGS. 3 thru 10, plate 20 will be described in detail. Plate 20 is generally comprised of a top (cephalad) portion 40, a bottom (caudal) portion 60, and a bridge portion 80. Moreover, plate 20 has an anterior side 22, a posterior side 24, a lateral side 26, a medial side 28, and upper and lower sides 30A, 30B. Plate 20 has a length which is at least sufficient to enable plate 20 to connect at least two vertebrae. However, it will be appreciated that the length of the plate in any particular installation will depend upon the condition to be corrected and the number of vertebrae to be held in a desired spatial relationship relative to each other by plate 20.

Figure 10:
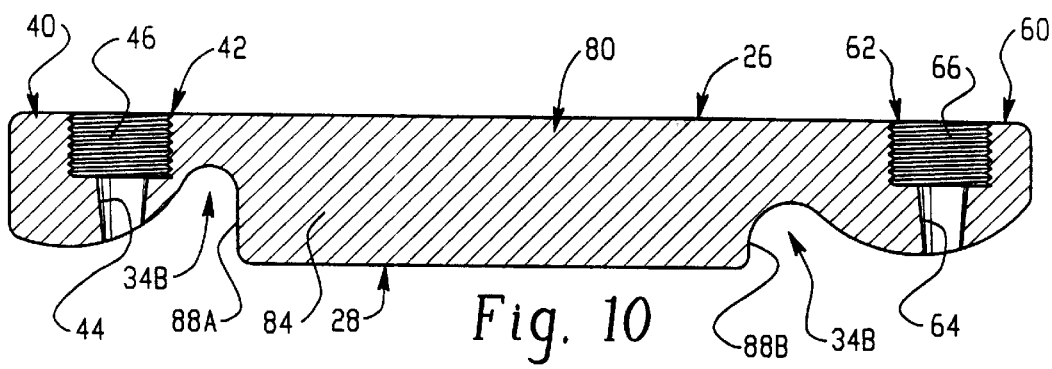
FIG. 10 is a sectional view of the bone plate, taken along line 10—10 of FIG. 9.

Top portion 40 includes a pair of generally circular openings 42, which are dimensioned to receive fastener means, namely, bone screw 100 and set screw 140. Each circular opening 42 has a tapered section 44 and a threaded section 46, as best seen in FIG. 10. Tapered section 44 is generally concentric with threaded section 46. Tapered section 44 has a taper (e.g., Morse taper) extending from a first end adjacent to threaded section 46 to a second end terminating at medial side 28. The taper formed in circular opening 42 matches a mating taper formed on screw 100, as will be explained in detail below in connection with FIG. 11. Threaded section 46 includes threads that mate with threads formed on set screw 140, as will also be explained below.

Tapered section 44 has a diameter which is smaller than the diameter of the adjacent threaded section 46. As a result, an annular shoulder 48 is formed at the interface between tapered section 44 and threaded section 46. Set screw 140 is driven against the top of screw 100, thus forcing screw 100 into tapered section 44.

Figure 8:
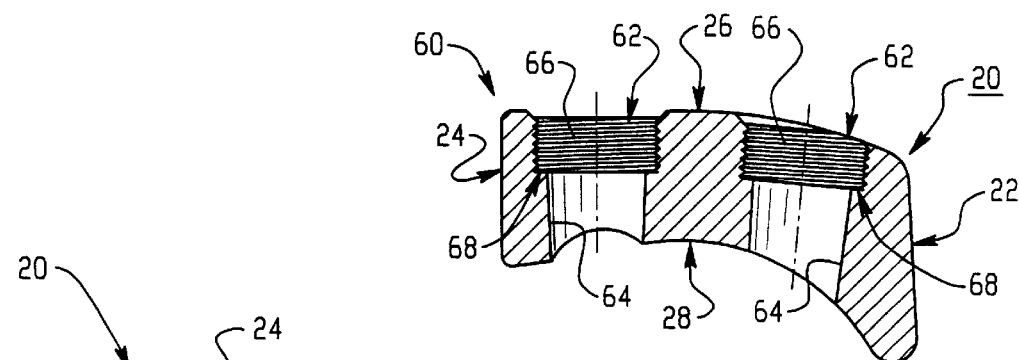
FIG. 8 is a sectional view of the bone plate, taken along line 8—8 of FIG. 7.
Figure 9:
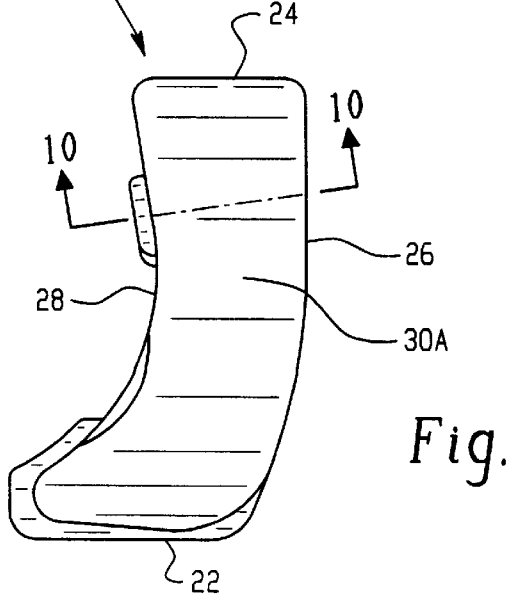
FIG. 9 is an end view of the bone plate.

Bottom portion 60 is similar to top portion 40. Bottom portion 60 includes a pair of generally circular openings 62, which are dimensioned to receive fastener means, namely, screw 100 and set screw 140. Each circular opening 62 has a tapered section 64 and a threaded section 66. Tapered section 64 is generally concentric with threaded section 66. Tapered section 64 tapers from a first end adjacent to threaded section 66 to a second end terminating at medial side 28 (FIGS. 8 and 10). The taper formed in circular opening 62 matches a mating (Morse) taper formed on screw 100, as will be explained below in connection with FIG. 11. Threaded section 66 includes threads that mate with the threads formed on set screw 140, as will also be described below.

Tapered section 64 has a diameter which is smaller than the diameter of the adjacent threaded section 66. As a result, an annular shoulder 68 is formed at the interface between threaded section 66 and tapered section 64. Set screw 140 is driven against the top of screw 100, thus forcing screw 100 into tapered section 64.

It should be appreciated that generally circular openings 42, 62 could be replaced with a plurality of elongated slots.

Bridge portion 80 interconnects top portion 40 and bottom portion 60, and is dimensioned to span an intervertebral space. It is understood that bridge portion 80 can be lengthened or shortened depending upon the total length of plate 20 required for the particular vertebral anatomy. Bridge portion 80 is generally comprised of an anterior wall 82 and posterior wall 84. Anterior wall 82 and posterior wall 84 extend downward from lateral side 26 and act as "struts." It should be appreciated that the length and width of walls 82, 84 may vary. A recess 90 is defined by anterior wall 82, posterior wall 84, and top and bottom portions 40, 60. Recess 90 provides an observation window in plate 20. The observation window allows interoperative graft access and postoperative graft evaluation (i.e., visualization of the healing process in the bone graft) from a lateral X-ray. Graft is not obscured radiographically from any standard view. As illustrated in FIGS. 1–3 and 5–7, recess 90 has a generally elliptical or oval shape. However, it will be appreciated that recess 90 may have varying geometries, including a rectangle, a square, an oval, a parallelogram, or an irregular shape. Moreover, recess 90 could be comprised of a plurality of smaller recesses or holes. Recess 90 could also narrow inward toward the center region to allow visualization of the edges of a graft.

Furthermore, other types of observation windows may be formed in plate 20. In this regard, one or more suitable openings may be formed in walls 82 and 84 to provide improved anterior-posterior plane visualization. Other embodiments include an observation window formed of solid material, wherein the material is radiolucent, such as a carbon-fiber reinforced polyaryletherketone polymer, and an observation window which has a cap or lid that may be attached to the plate to retain and/or compress graft.

Gaps or notches 34A are formed between anterior wall 82 and top and bottom portions 40, 60. Likewise, gaps or notches 34B are formed between posterior wall 84 and top and bottom portions 40, 60. The gaps or notches 34A bounding anterior wall 82 define a ledge 86A at the upper end of anterior wall 82, and a ledge 86B at the lower end of anterior wall 82. Likewise, the gaps or notches 34B bounding posterior wall 84 define a ledge 88A at the upper end of posterior wall 84, and a ledge 88B at the lower end of posterior wall 84.

Referring now with particular reference to FIGS. 3 and 4, the gaps or notches 34A, 34B are dimensioned to receive a portion of a vertebral body. Ledges 86A, 86B, 88A and 88B provide support surfaces that protrude into the corpectomy space, so that the endplates of the adjacent vertebral bodies rest on at least one ledge at either end of plate 20 (FIG. 4). It should be noted that suitable graft material will fill the gap between vertebral bodies $V_1$ and $V_2$. The graft material has been omitted from FIGS. 3 and 4 so as to more clearly illustrate the present invention It should be understood that ledges 86A, 88A, and ledges 86B, 88B may be respectively spaced apart from each other by various dimensions. This may allow plate 20 to be used after a corpectomy procedure or after a discectomy procedure. The ledges may extend the full width of the vertebral body. In such case, a pair of "struts" may be connected to each other, effectively forming an intervertebral cage device as an integral unit to the plate. According to alternative embodiments of the present invention, plate 20 could have ledges which are composed of bioresorbable compound (e.g., poly-lactic acid), a bone graft, or a bone graft substitute material. In yet another embodiment of the present invention all of the ledges could be omitted to form a plate which has a flatter, generally planar profile.

It should be appreciated that medial side 28 has an outer surface that is anatomically contoured to match the profile of aspects common to vertebral bodies (e.g., thoracic and lumbar vertebrae). The surface of medial side 28 is contoured to fit the vertebrae. Accordingly, the anterior portion of the medial side surface is relatively curved. The posterior portion of the medial side surface is generally flat in cross-section. Furthermore, as indicated above, plate 20 has gaps or notches 34A, 34B which are dimensioned to receive a portion of the vertebral bodies. The above-mentioned properties allow: (1) plate 20 to have a low profile (i.e., plate 20 sits "down into," rather than "on top of" the bone), (2) bio-mechanical load-sharing, which increases the mechanical properties of fixation system 10 (i.e., stiffness, strength and fatigue life), and (3) faster implantation times, as will be explained in detail below.

It will be appreciated that the surface of medial side 28 may have a varied geometry (e.g., engagement members) to allow fitting into the waist(s) of the vertebral bodies, such as steps, spines or teeth. Moreover, the surface of medial side 28 may be formed so as to bite into a bone at the waist of the vertebral bodies, such as with a spike or sharp tooth. Furthermore, the surface of medial side 28 may have a surface treatment which allows bone ingrowth, such as plasma spray, bead-sintering, knurling, hydroxyapatite, bioactive material, a plurality of small holes, roughened or otherwise irregular surfaces.

Screws 100 will now be described in detail with reference to FIGS. 1–2 and 11–12. Each screw 100 is generally comprised of threaded portion 102 and a head portion 110. Threaded portion 102 extends from the lower end of head portion 110 to rounded tip 106. Threads 104 are formed along the length of threaded portion 102. Threaded portion 102 is screwed into a vertebral body $V_1$, $V_2$, as will be explained below.

Figure 11:
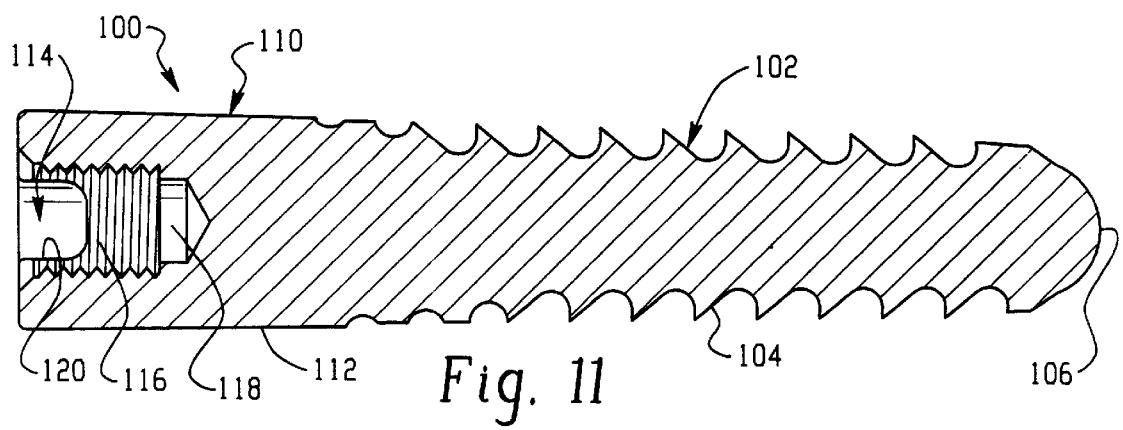
FIG. 11 is a sectional view of a screw, taken along line 11—11 of FIG. 12.
Figure 12:
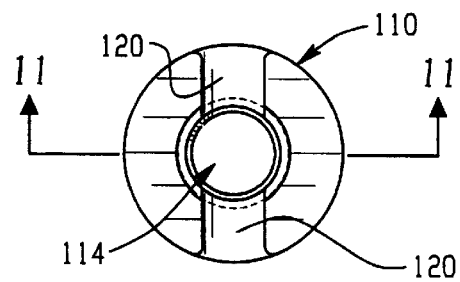
FIG. 12 is a top view of the screw shown in FIG. 1.
Figure 13:
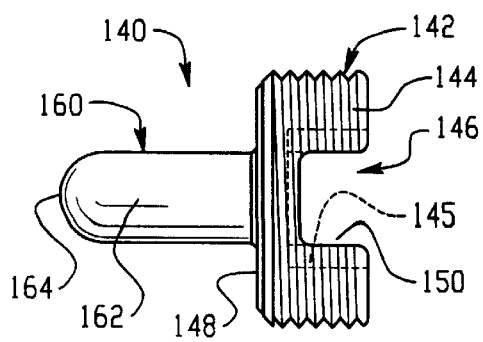
FIG. 13 is a side view of a set screw shown in FIG. 1.
Figure 14:
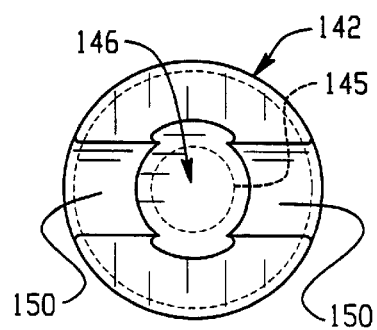
FIG. 14 is a top view of the set screw shown in FIG. 1.

Head portion 110 includes a tapered outer surface 112 and a recess 114, as best seen in FIG. 11. Tapered outer surface 112 tapers from the top of head portion 110 to the adjacent threaded portion 102. The taper of outer surface 112 matches the taper formed in tapered sections 44 and 64 of plate 20. The mating tapers align screw 20 with circular openings 42, 62, minimize local stress concentration, and provide pull-out resistance.

Recess 114 has a threaded section 116 and an inner recess section 118. Threaded section 116 has a radius greater than the radius of inner section 118. Notches 120 are formed in head portion 110. Recess 114, threads 116 and notches 120 are dimensioned to interface with a conventional instrument (e.g., a screw driver with a draw rod) for rotating screw 100. It should be understood that head portion 110 may take other forms suitable for interfacing with other types of instruments for rotating screw 100. Moreover, it should be appreciated that other types of suitable fastening devices may be substituted for screws 100.

In a preferred embodiment of the present invention, screws 100 have a diameter of approximately 7.0 mm, and have a length in the range of approximately 30 mm to 60 mm.

It will be appreciated that screw 100 may have other suitable geometries. For instance, the tapered head could be replaced by a spherical head. The spherical head would allow variable screw angulation. Other suitable alternative geometries include a screw with a flat or oval head which could be captured by a set screw. Moreover, the head of the screw could have a diameter greater than the opening in the bone plate, such that the head of the screw sits on top of the bone plate.

Set screw 140 will now be described with reference to FIGS. 1–2 and 13–14. Set screws 140 are generally comprised of a head portion 142 and a "dog point" or alignment member 160 integral therewith. Head portion 142 includes a threaded outer surface 144, a recess 146 and a front face 148. Threaded outer surface 144 has threads that mate with the threads of threaded sections 46 and 66 of plate 20. In a preferred embodiment of the present invention, head portion 142 has an outer diameter of approximately 9.5 mm. Recess 146 has internal threads. Moreover, notches 150 are formed at the upper end of head portion 142. Similar to the head portion 110 of screw 100, recess 146, threads 145 and notches 150 are dimensioned to interface with a conventional instrument (e.g., a screw driver with a draw rod) for rotating set screw 140. It should be understood that head portion 142 may take other forms suitable for interfacing with other types of instruments for rotating set screw 142.

Alignment member 160 is integrally attached to head portion 142 at front face 148. According to a preferred embodiment, alignment member 160 includes a generally cylindrical elongated portion 162 and a full spherical radius tip 164 at the distal end thereof. It will be appreciated elongated portion 162 may have other suitable geometries (e.g., hex, square, etc.). Moreover, tip 164 may be flat or have other suitable geometries.

It will be appreciated that set screw 140 may have alternative configurations. In this regard, the alignment member could have a non-circular shape or a sharp tip. In another embodiment alignment member 160 may be omitted from set screw 140, thus providing a set screw with a generally planar front face. Moreover, the alignment member 160 could be omitted and replaced with a hole extending through the entire set screw. In this case, the alignment member (e.g., dog point) could be located on the driving instrument. In yet another embodiment, a cannulated (i.e., tubular) bone screw could be used with a set screw that is aligned by driving it along a wire inserted through the bone screw (and also through the set screw).

In a preferred embodiment of the present invention, set screw 140 has a diameter of approximately 9.5 mm.

It will be appreciated that in an alternative embodiment of the present invention, set screws 140 could be replaced by other suitable locking mechanisms.

Both screws 100 and set screws 140 are preferably made of implant grade titanium alloy (Ti-6Al-4V (ELI) per ASTM F-136), or other biocompatible material, such as stainless steel, carbon fiber reinforced polyaryletherketone composites and the like.

It should be appreciated that screws 100, set screws 140, and the respective screw and set screw interfaces formed in plate 20 (i.e., screw-plate interface) are suitable for use with other similar connecting devices, including hooks, rod connectors, ligament anchors, and the like.

Moreover, it should be appreciated that the screws, set screws, and screw and set screw interface formed in plate 20 may take various alternative forms. For instance, a slightly offset set screw could be used to provide the locking force. In yet another embodiment, the plate could be arranged with only a taper interface for receiving only tapered-head screws, without the use of any set screws. Other alternatives, include the use of a press fit mechanism in which a screw is driven into an undersized hole formed in the plate. As a result, locking is provided by material deformation. In yet another embodiment, an alternative locking screw geometry, such as a spherical-head screw with a set screw driven directly down onto them could be employed. Such an arrangement could provide a variable-screw angle system. Another option is to provide a screw with slots or holes arranged to correspond to similar geometries formed on the plate. The holes could be filled with bone cement or similar material to prevent screw movement, in lieu of a set screw. Other alternatives include a set screw which compresses more than one screw to provide locking, and a plate which has a plurality of slots for variable screw placement.

As indicated above, fixation system 10 is particularly well suited for the treatment of thoraco-lumbar spinal instability caused by such conditions as trauma, tumor, severe disc degeneration, and anterior fusion following multiple posterior operations including pseudoarthrosis. A brief summary of the preferred surgical technique will now be described.

Prior to installation, medial-lateral and anterior-posterior X-rays, CT scans, and MRI images may be useful in determining angular deformity, degree of canal compromise, and potential instability. Moreover, such images may also be useful to approximate the correct size of plate 20 and length of screw 100.

The patient undergoing treatment is positioned in a lateral decubitus position. Preferably, a retroperitoneal or combined thoraco-lumbar surgical approach is used. Next, the spine is exposed one level above and one level below the damaged segment. The site is then prepared by removing the disc material adjacent to the damaged vertebrae. A vertebral body distractor is placed inside the site, against the caudal endplate of the cephalad body and the cephalad endplate of the caudal body. A distraction sufficient to assist in the corpectomy procedure is then applied. Following distraction a corpectomy procedure is performed.

Graft placement is carried out by: (1) measuring the medial-lateral width of the vertebral bodies to determine the screw length required, (2) measuring the graft site, (3) harvesting and shaping an autologous tri-cortical iliac crest graft to fit within the site created, (4) determining the appropriate plate size by comparison to the graft site measurement, (5) placing the graft, (6) removing the vertebral body distractor, and (7) placing additional morselized graft anterior to the strut graft, if needed.

Installation of fixation system 10 will now be described with particular reference to FIGS. 1–4. After the graft has been properly sized and an appropriate sized plate 20 has been selected, plate 20 will fit into the narrow waist of the adjacent vertebral bodies. At least one ledge of 86A and 88A, and one ledge of 86B and 88B, should contact each adjacent vertebral body. This allows the load to be transferred through the "struts" (i.e., walls 82 and 84) of plate 20, rather than through screws 100. It should be noted that unusual anatomy may require some bone material to be removed to allow plate 20 to seat properly on the vertebral body.

Next, a first hole is created at the posterior caudal location. An awl cannula is inserted into the appropriate circular opening 42, 62 in plate 20. The awl shaft is then inserted through the awl cannula. The lateral cortex is punctured by firmly pushing down on the awl shaft. As an alternative procedure, the awl shaft may be screwed onto the awl cannula, and the awl is then used as a one-piece instrument. However, this may cause difficulty in creating a properly aligned hole, which in turn may cause difficulty in placing screws 100.

A first screw 100 is then driven into the bone. In this regard, a screw 100 is loaded onto the driver using a flat-ended draw rod. Turning the draw rod clockwise will pull screw 100 firmly against the driver. Screw 100 is then driven into the bone. However, screw 100 is not fully tightened. This prevents the opposite end of plate 20 from lifting off the bone slightly, making it difficult to place subsequent screws. Proper screw length should be verified, either radiographically or by direct palpation. At least one full thread should engage the contralateral cortex. It should be appreciated that the driving tapered head 112 of screw 100 into mating tapered section 44, 64 of plate 20, forces proper alignment between screw 100 and plate 20, provides "pull-out" resistance, and evenly distributes stresses on both screw 100 and plate 20. The latter may significantly affect the fatigue life of screws 100.

The above steps are repeated for the remaining screws 100. The second screw inserted should be the other posterior side location. The third and fourth screws should be the remaining anterior side locations. None of the screws should be completely tightened until all of the screws have been inserted.

Next, set screws 140 are loaded onto the driver. Alignment member 160 of set screw 140 is inserted into recess 114 of screw 100 to aid in locating set screw 140 and prevent cross-threading. Alignment member 160 forces an orthogonal alignment of threaded outer surface 144 and mating threaded section 46, 66 of plate 20. It should be appreciated that the radius of threaded section 116 is larger than the radius of alignment member 160. Set screws 140 are preferably tightened to approximately 60 inch-pounds. It should be noted that set screws 140 may be inserted into circular openings 42, 62 in any sequence desired.

It should be appreciated that driving set screws 140 on top of screws 100 forces screws 100 deeper into tapered section 44, 64, and prevents screws 100 from moving. As a result, the set screws have effectively turned an all-screw construct into an all-bolt construct.

Following installation, the wound is closed, and post-operative procedures are implemented.

As indicated above, plate 20 itself is contoured to fit the lateral profile of the thoraco-lumbar vertebrae. Since the primary use of the present invention is some form of a corpectomy or discectomy procedure, plate 20 takes advantage of the removed bone medial to the implant. The added thickness provides for better rigidity for plate 20, and allows for ledges 86A, 86B, 88A, 88B that are able to support the vertebrae in direct compression. Since the material is added into the corpectomy space, the profile of the construct is lower, as compared to prior art plate designs.

The present invention also provides significant improvements in stiffness and stress. Computer simulations show plate 20 to be approximately 7X to 10X stiffer than prior art plates. Moreover, the maximal stress concentrations of plate 20 were found to be approximately ¼ to ¾ the maximal stress concentrations of prior art plates.

As indicated above, plate 20 is anatomically fitted to the vertebral bodies. Consequently, a significant portion of the stress will be transferred directly to plate 20, rather than through screws 100. Plate 20 supports vertebral bodies in a manner similar to a corpectomy cage. Such loading condition shields screws 100, thus extending their fatigue life.

The present invention provides an enhanced screw-plate interface. As indicated above, the head portion of screws 100 have a taper, which matches a taper on plate 20. The mating tapers prevent screws 100 from backing out once tightening force is applied. In addition, set screws 140 are driven into plate 20 directly on top of screws 100, thus preventing any noticeable movement.

It should be appreciated that plate 20 may take other suitable forms. For instance, plate 20 could have a generally flat profile, thus virtually eliminating the downward extending walls 82 and 84 and corresponding ledges 86 and 88. Moreover, plate 20 could be modified to receive only a screw, rather than a screw and a set screw.

Figure 15:
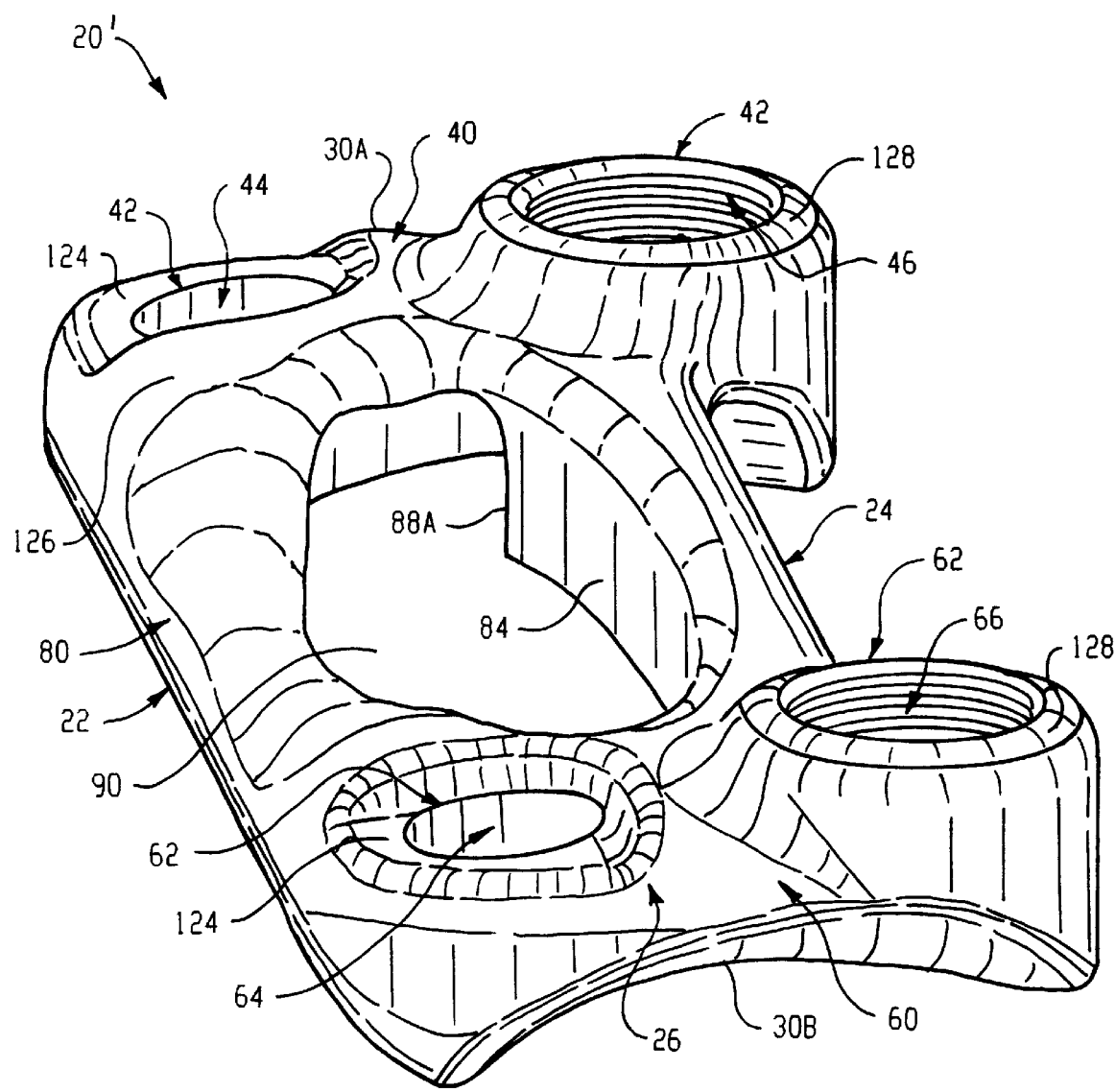
FIGS. 15 and 16 are perspective views of a bone plate according to an alternative embodiment of the present invention.
Figure 16:
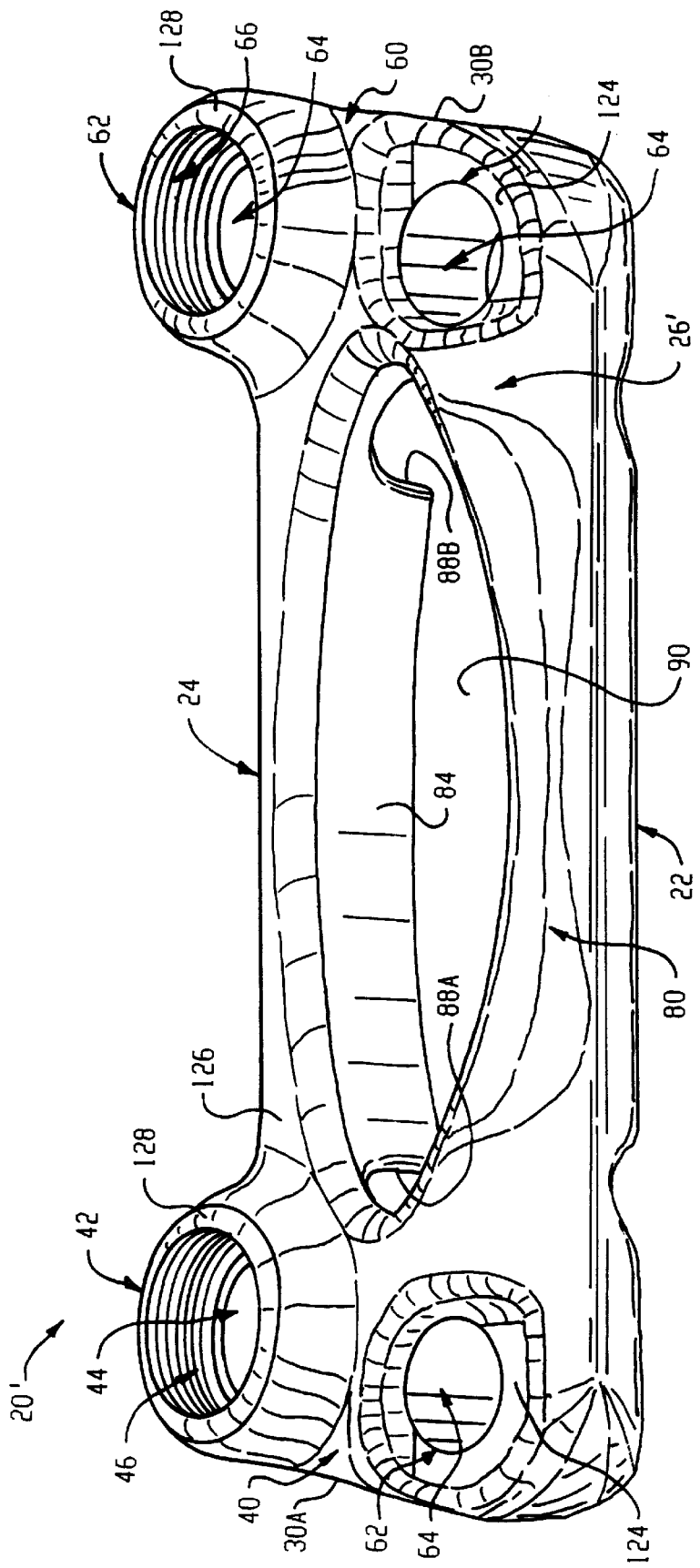
Figure 17:
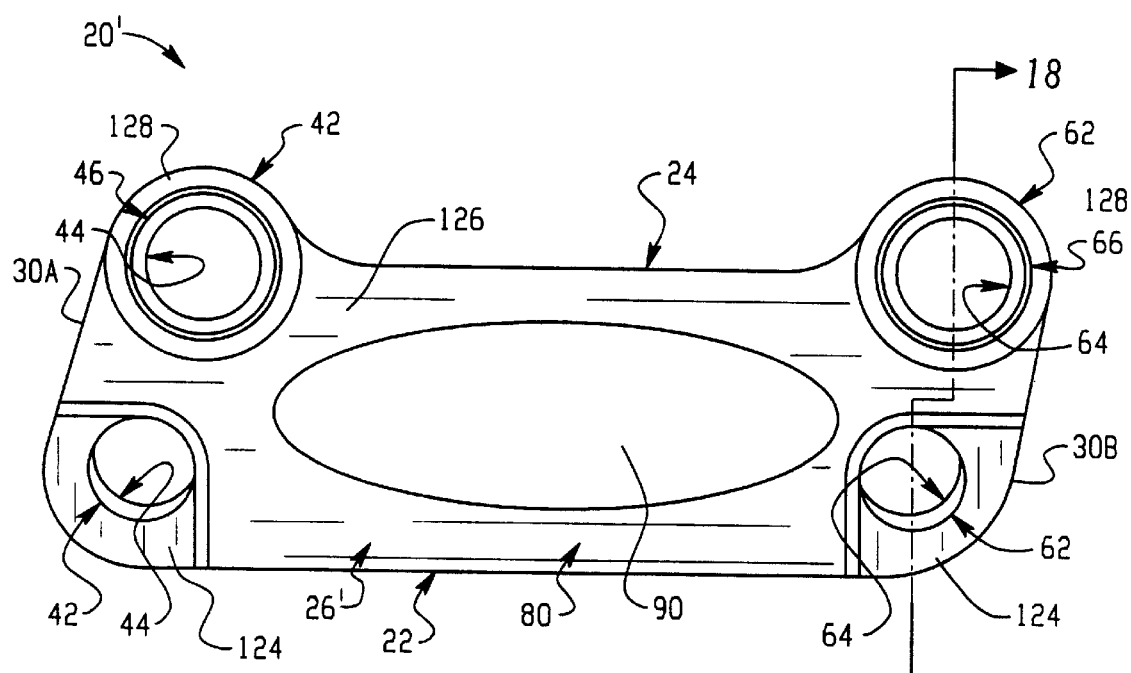
FIG. 17 is a top plan view of the bone plate shown in FIGS. 15 and 16.
Figure 18:
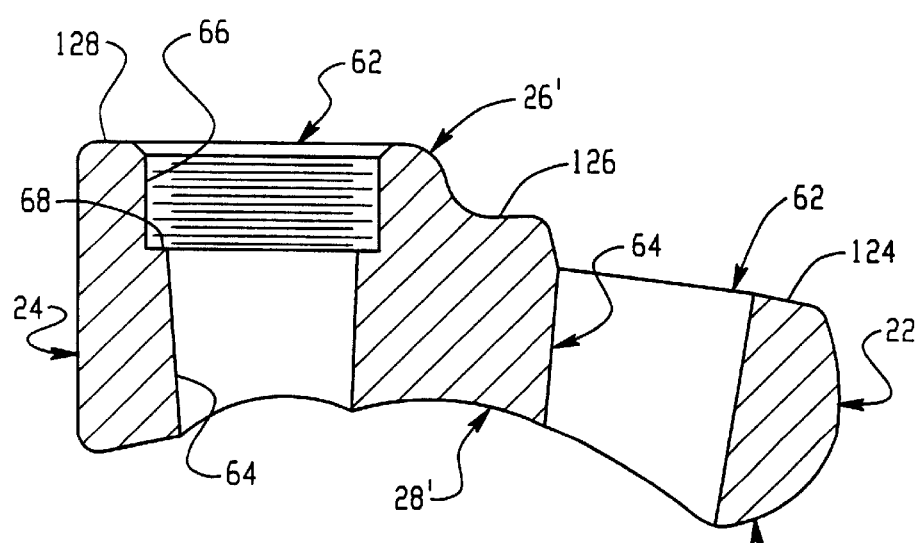
FIG. 18 is a cross-sectional view of the bone plate, taken along line 18—18 of FIG. 17.
Figure 19A:
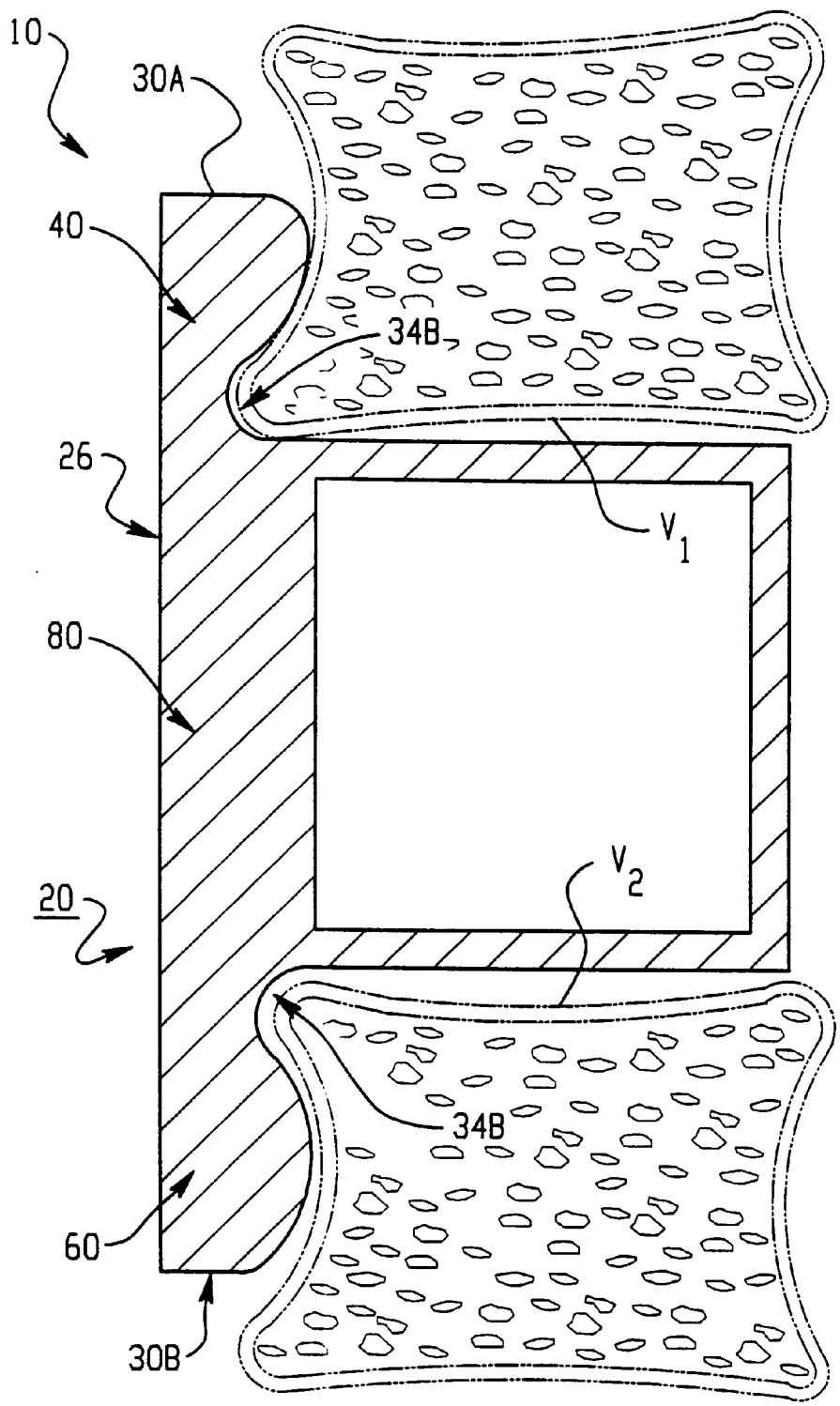
FIG. 19A is a posterior sectional view of the bone fixation system, as affixed to a pair of vertebral bodies, showing the ledge members connected together to form an intervertebral cage.
Figure 19B:
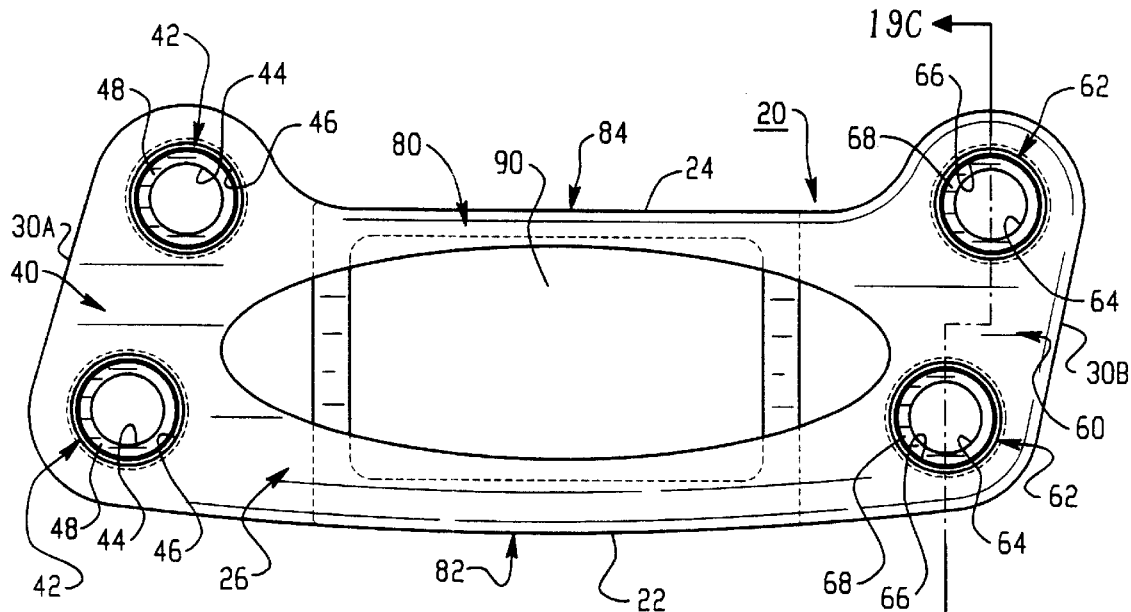
FIG. 19B is a top plan view of the lateral side of the bone plate, showing the ledge members connected together to form an intervertebral cage.
Figure 19C:
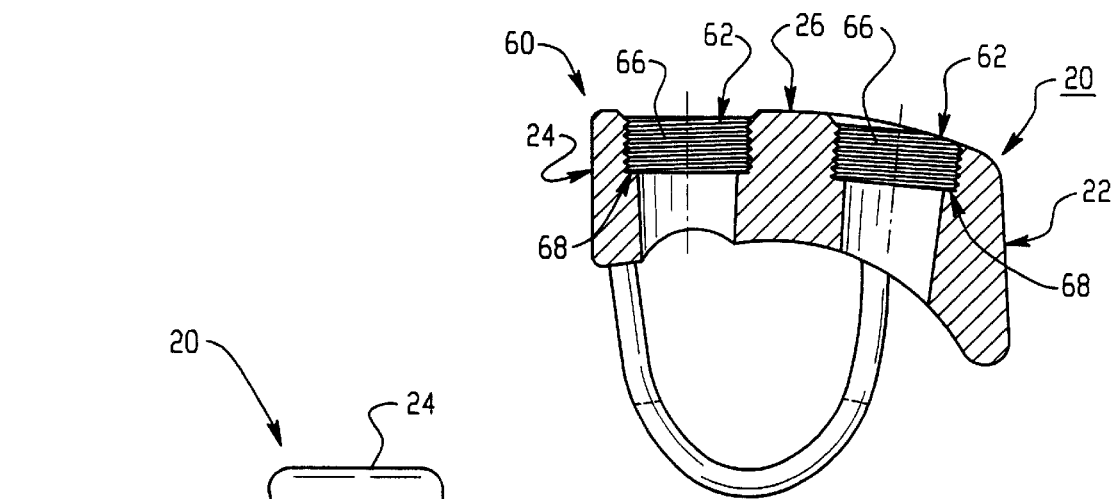
FIG. 19C is a sectional view of the bone plate, taken along line 8—8 of FIG. 19B, showing the ledge members connected together to form an intervertebral cage.
Figure 19D:
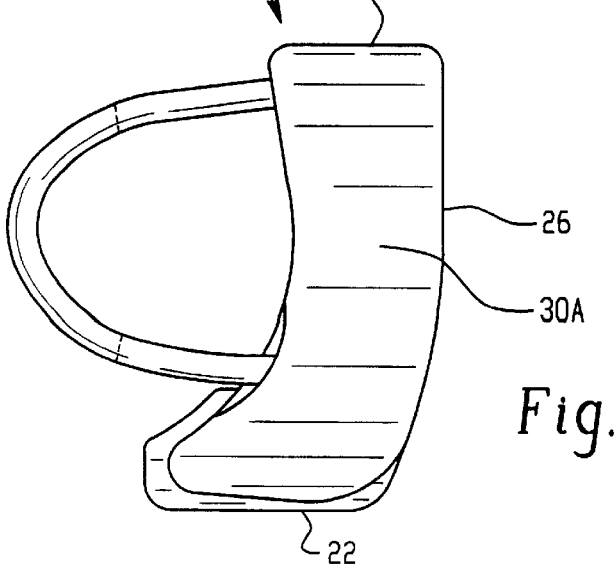
FIG. 19D is an end view of the bone plate, showing the ledge members connected together to form an intervertebral cage.
Figure 19E:
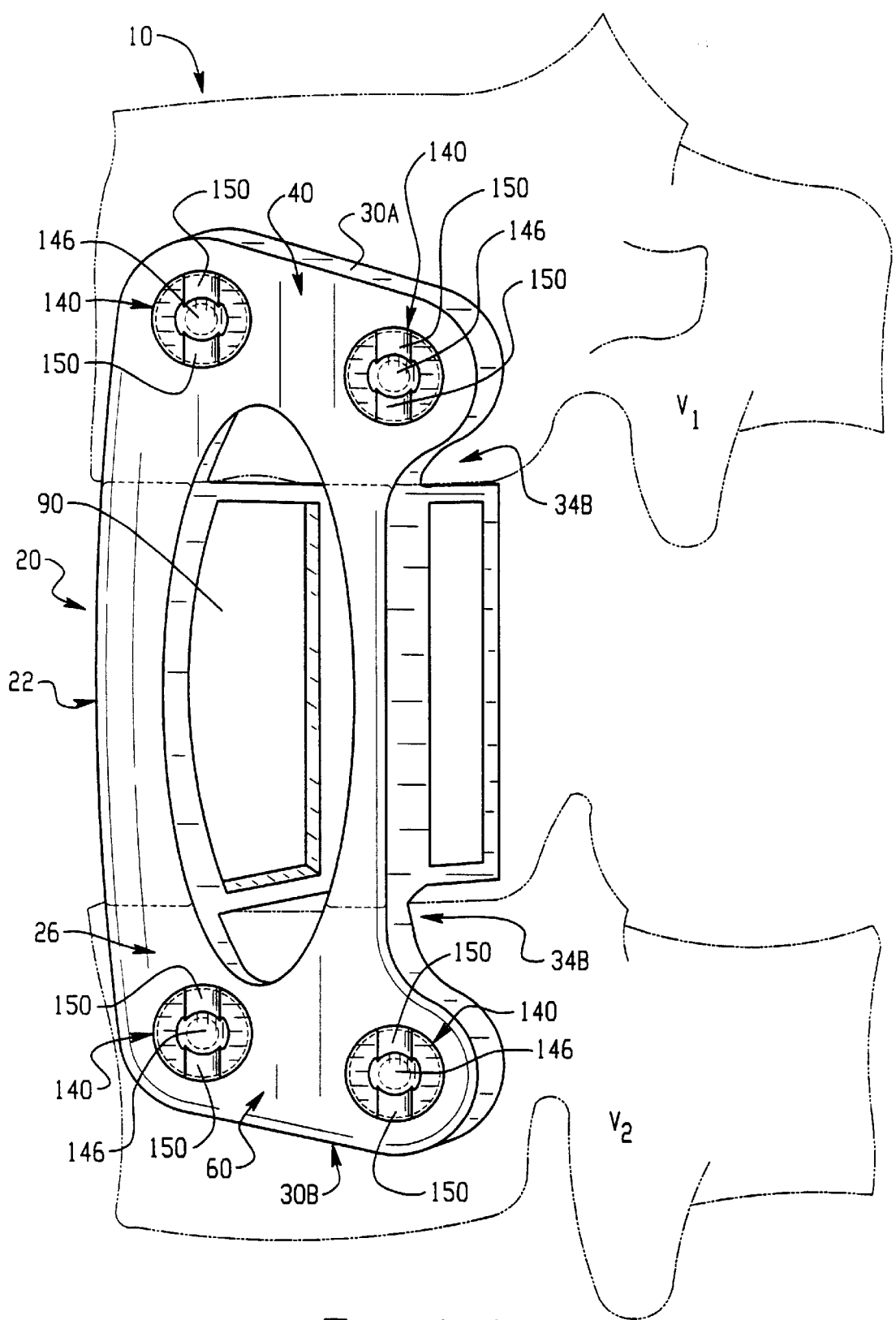
FIG. 19E is a lateral side view of the bone fixation system, as affixed to a pair of vertebral bodies, showing the ledge members connected together to form an intervertebral cage.
Figure 20:
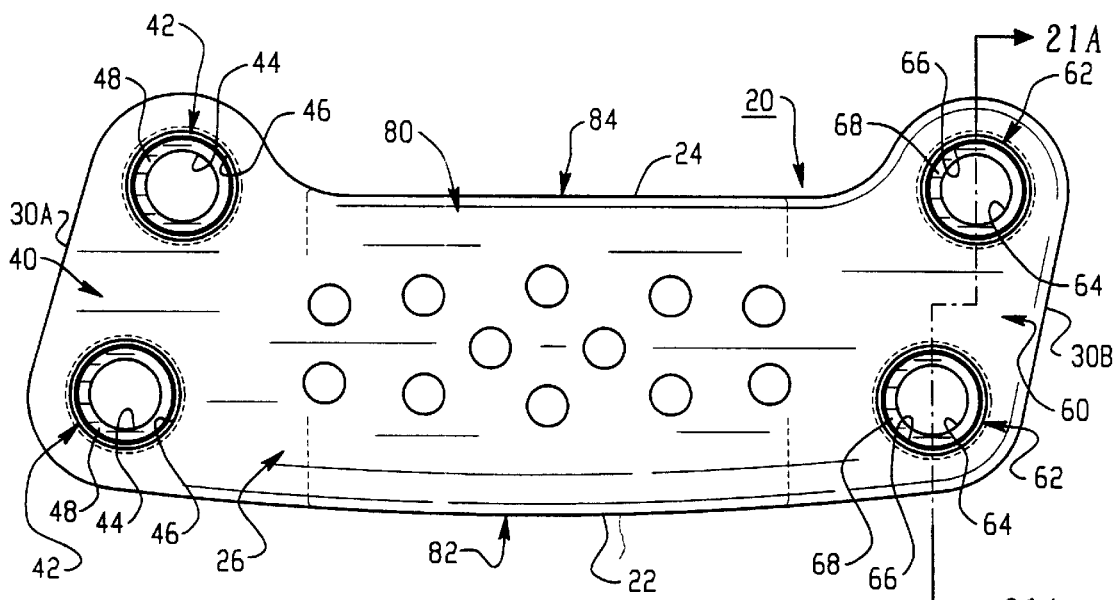
FIG. 20, is a top plan view of the lateral side of the bone plate, showing a window having a plurality of holes.
Figure 21A:
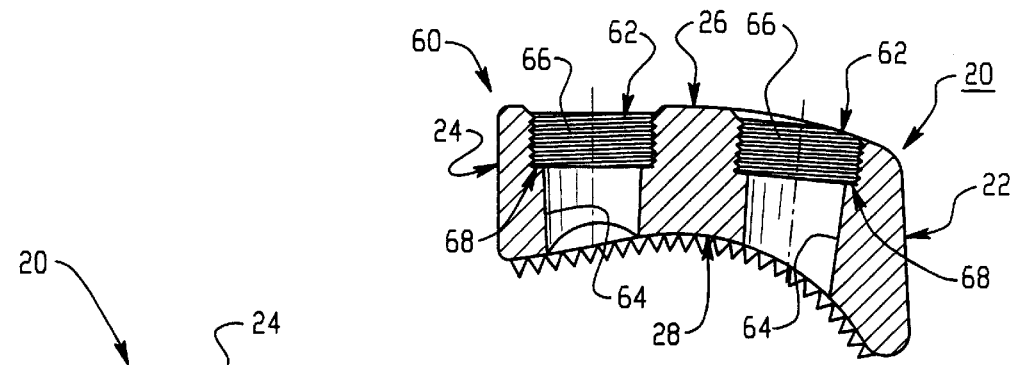
FIG. 21A is a sectional view of the bone plate, taken along line 8—8 of FIG. 20, showing an engagement structure comprising teeth.
Figure 21B:
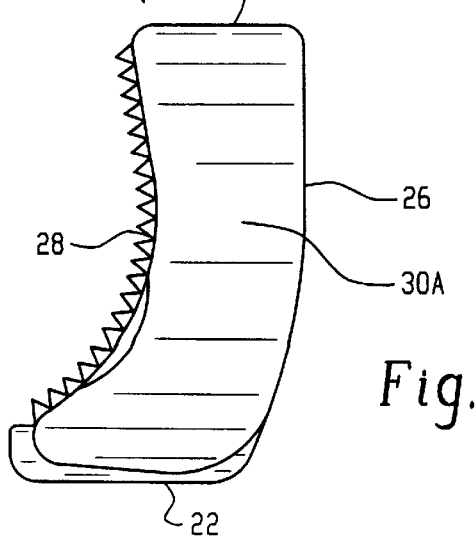
FIG. 21B is an end view of the bone plate, showing an engagement structure comprising teeth.
Figure 21C:
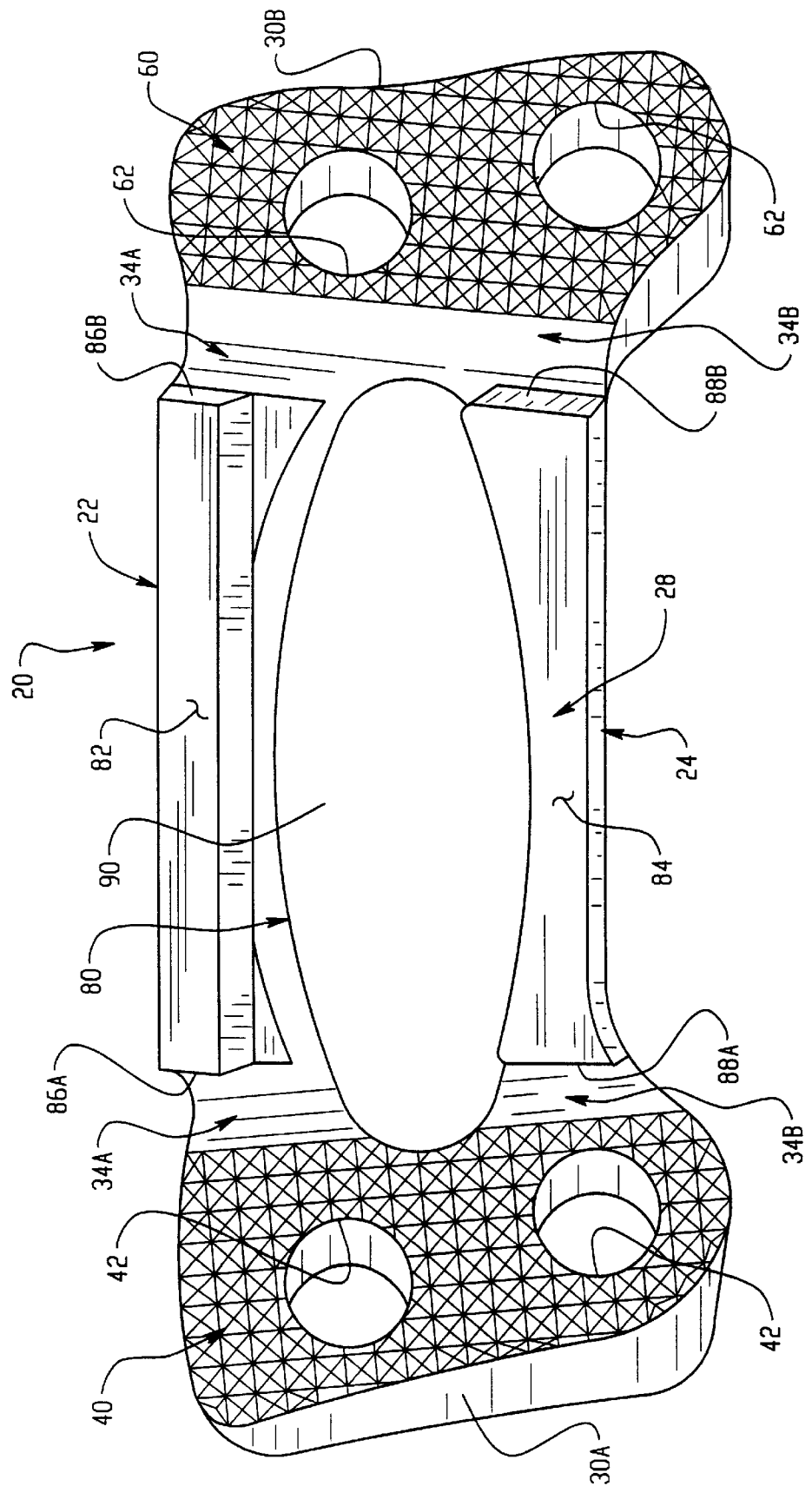
FIG. 21C is a medial side view of the bone plate shown in FIG. 5, showing an engagement structure comprising teeth.
Figure 21D:
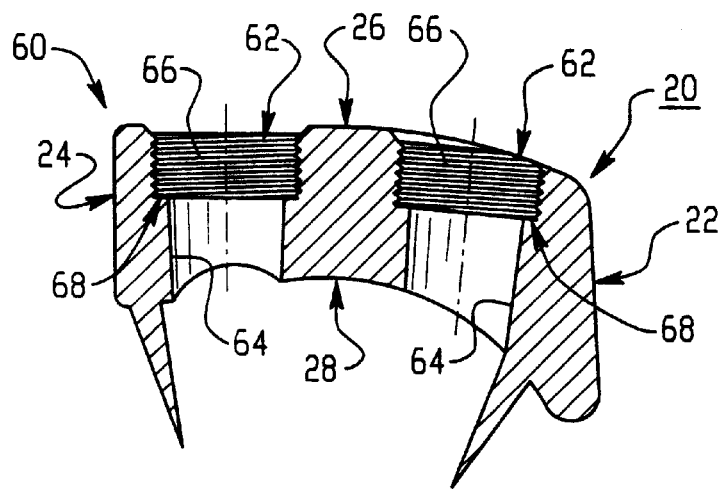
FIG. 21D is a sectional view of the bone plate, taken along line 8—8 of FIG. 20, showing an engagement structure comprising spikes.
Figure 21E:
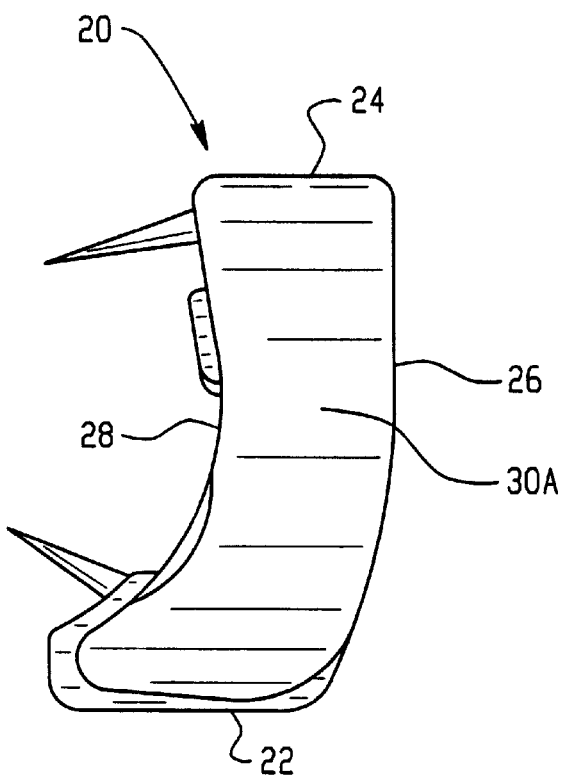
FIG. 21E is an end view of the bone plate, showing an engagement structure comprising spikes.
Figure 22:
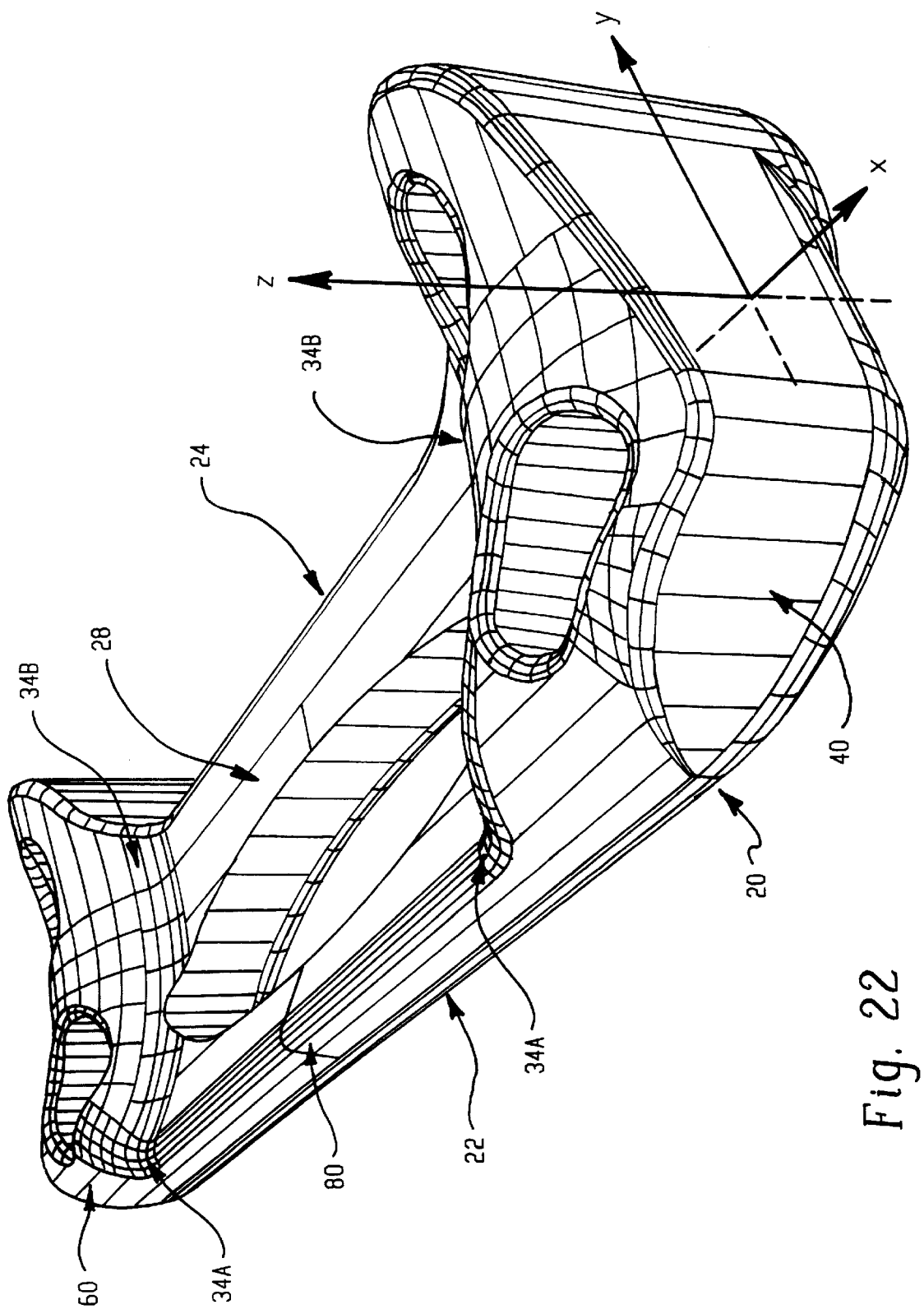
FIG. 22 is a perspective view of a bone plate, taken from an anterior side perspective, showing the three-dimensional medial surface contours at top and bottom portions of the preferred embodiment and showing an alternative embodiment of support structure.
Figure 23:
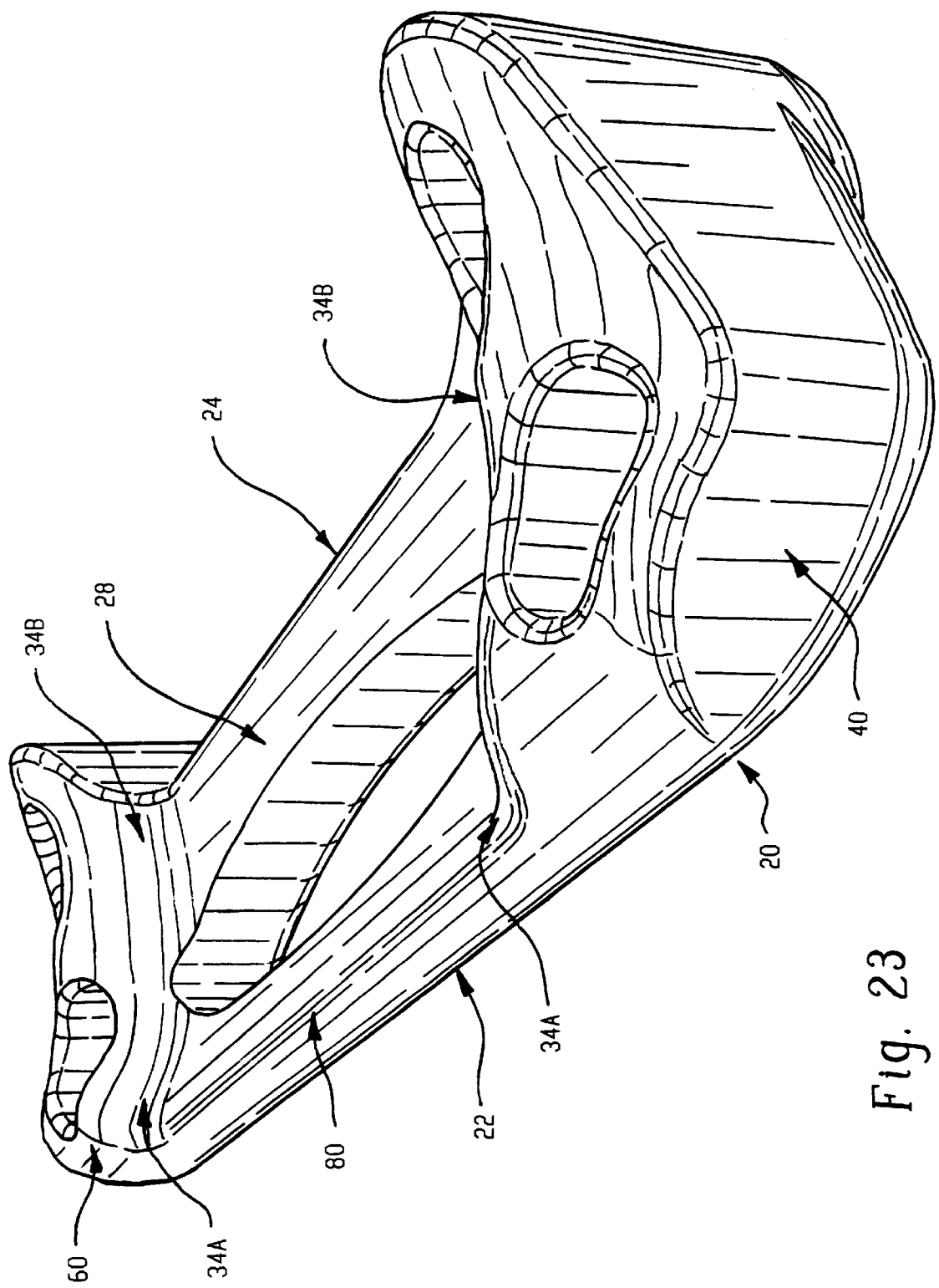
FIG. 23 is the perspective view of FIG. 22 shown as a three-dimensional surface model.
Figure 24:
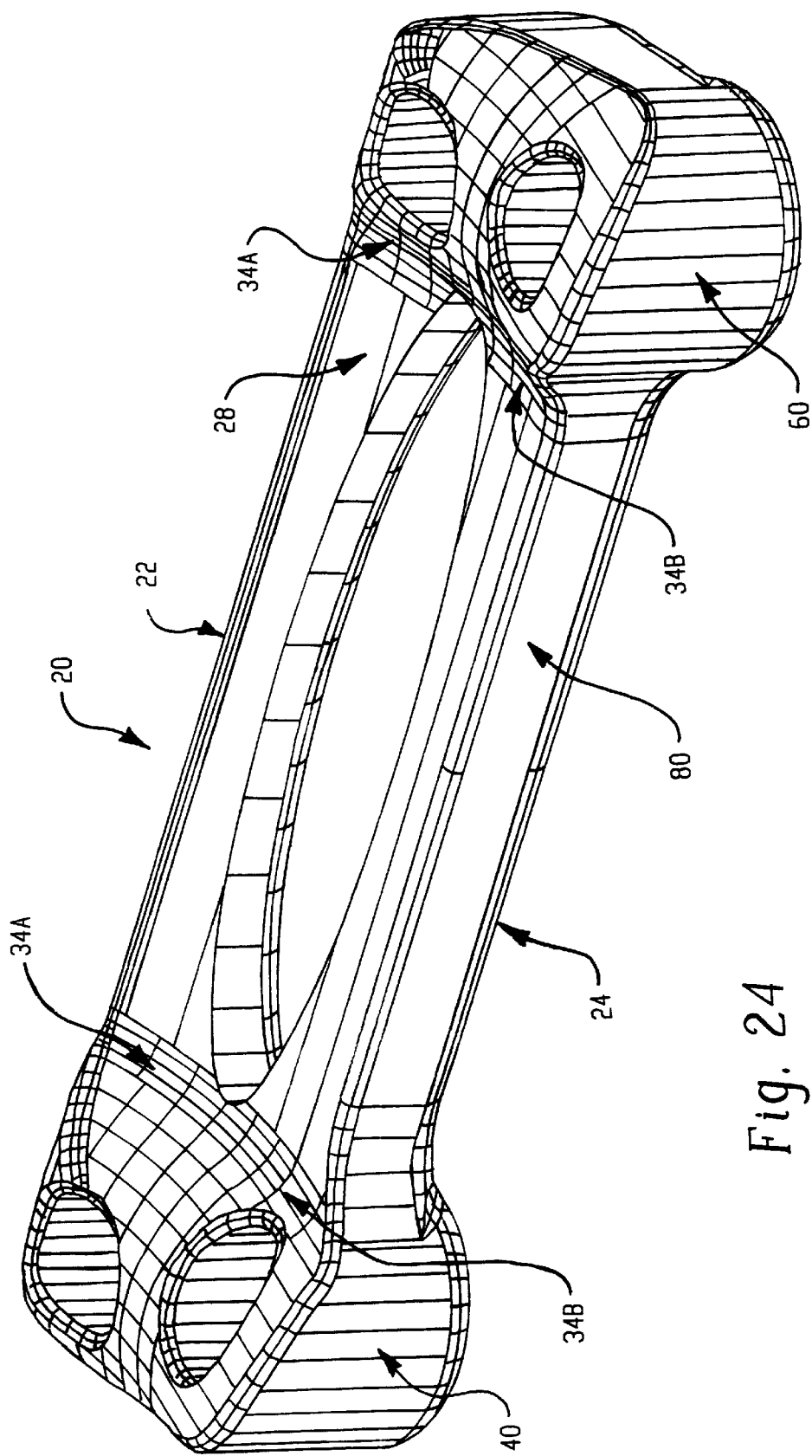
FIG. 24 is a perspective view of a bone plate, taken from a posterior side perspective, showing the three-dimensional medial surface contours at top and bottom portions of the preferred embodiment and showing an alternative embodiment of support structure.
Figure 25:
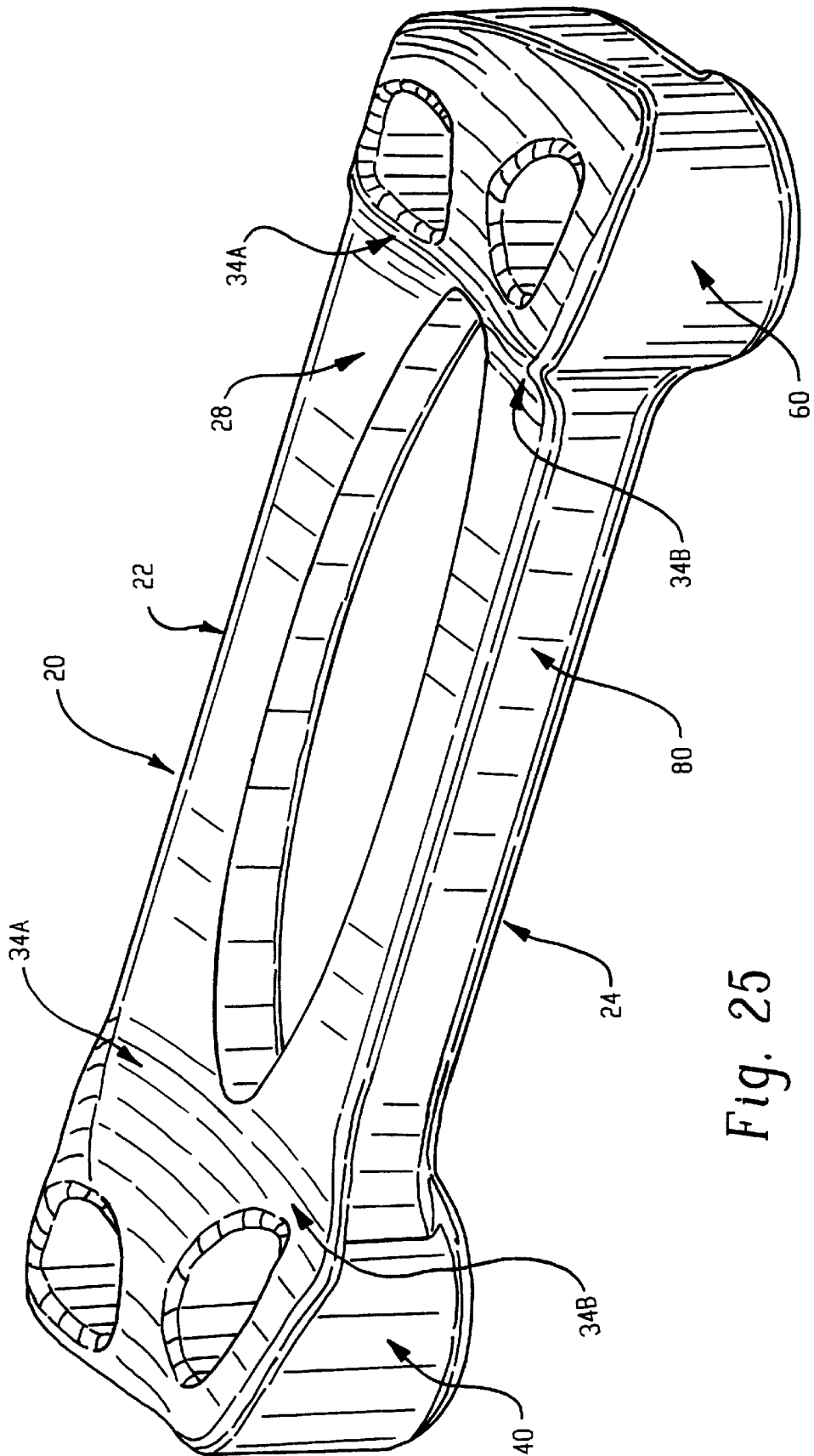
FIG. 25 is the perspective view of FIG. 24 shown as a three-dimensional surface model.

Turning now to FIGS. 15–18, an alternative embodiment of the bone plate will be described. Bone plate 20' is similar in many respects to bone plate 20 described above. However, bone plate 20' reduces the amount of material needed to form the bone plate. Moreover, bone plate 20' has a reduced profile, which in turn is less intrusive to body tissue. In order to provide these features, the lateral side of the bone plate has been modified as shown in the figures. In particular, lateral side 26' has three primary surface levels. Lower surface 124 is located adjacent to the anterior side circular openings 42, 62. Upper surface 128 is located adjacent to the posterior side circular openings 42, 62. A middle surface 126 is located between lower surface 124 and upper surface 128. Middle surface 126 comprises the majority of lateral side 26', as best seen in FIG. 17. Generally sloping surfaces provide a transition between the lower, middle and upper surfaces, as best seen in FIGS. 15–16 and 18.

It should be appreciated that upper surface 128 is at the same general level as the surface of lateral side 26 of bone plate 20 (FIG. 8). Middle surface 126 and lower surface 124 are reduced from this level. The level of lower surface 124 is reduced to a level wherein the threaded sections of anterior side circular openings 42, 62 are removed. In this regard, anterior side circular openings 42, 62 include only a respective tapered section 44, 64. Consequently, no set screw 140 is used in connection with the anterior side circular openings 42, 62 of bone plate 20'. The top surface of head portion 110 of screw 100 is generally flush with lower surface 124, when bone plate 20' is appropriately installed. Posterior side circular openings 42, 62 are configured the same as those described in connection with bone plate 20.

It should also be noted that bone plate 20' has slightly modified medial side 28'. In this regard, a rounded corner portion 29 is formed at the anterior end of medial side 28' (FIG. 18). This differs from the protruding corner formed at the anterior end of medial side 28 of bone plate 20 described above (FIG. 8). Rounded corner portion 29 allows for yet more reductions in material.

The invention has been described with reference to a preferred embodiment. Obviously, modifications and alterations will occur to others upon a reading and understanding of this specification. It is intended that all such modifications and alterations be included insofar as they come within the scope of the appended claims or the equivalents thereof.

Having thus described the invention, it is now claimed:

1. A bone fixation system comprising:

a three-dimensionally contoured elongated plate having a top portion, a bottom portion, and a bridge portion integrally spanning between said top portion and said bottom portion, said top portion having a medial side comprising three dimensional surface contours extending substantially from an upper end of said top portion to said bridge portion and extending substantially from an anterior side of said top portion to a posterior side of said top portion, and said bottom portion having a medial side comprising three dimensional surface contours extending substantially from a lower end of said bottom portion to said bridge portion and extending substantially from an anterior side of said bottom portion to a posterior side of said bottom portion, said medial side of said top and bottom portions being contoured to anatomically fit both an anterior and a lateral profile of a bone structure;

at least one support structure having medial surface contours extending substantially from an anterior surface of said three-dimensionally contoured elongated plate to a posterior surface of said three-dimensionally contoured elongated plate, said medial surface contours capable of engaging external surfaces of bone structures; and a fastener for fastening said plate to said bone structures.

2. A bone fixation system according to claim 1, wherein said at least one support structure includes contoured gaps located adjacent to said top and bottom portions.

3. A bone fixation system according to claim 2, wherein said contoured gaps have support surfaces that are connected together to form an intervertebral cage device.

4. A bone fixation system according to claim 2, wherein said contoured gaps include at least one of: bioresorbable compound, bone graft, or bone graft substitute material.

5. A bone fixation system according to claim 1, wherein said bridge portion includes at least one window extending from a lateral side through a medial side of said bridge portion for observation of a graft area.

6. A bone fixation system according to claim 5, wherein said at least one window includes an opening having a general shape of: an ellipse, rectangle, square, oval or parallelogram.

7. A bone fixation system according to claim 5, wherein said at least one window includes a plurality of holes.

8. A bone fixation system according to claim 5, wherein said at least one window has an irregular shape.

9. A bone fixation system according to claim 1, wherein said top and bottom portions each include at least one opening dimensioned to receive said fastener.

10. A bone fixation system according to claim 9, wherein said at least one fastener opening includes a first fastener receiving section having a tapered surface, said fastener including a mating tapered surface, wherein said mating tapered surface generally matches the tapered surface of said first fastener receiving section.

11. A bone fixation system according to claim 10, wherein said fastener includes a set screw member having a threaded surface.

12. A bone fixation system according to claim 9, wherein said at least one opening includes a section dimensioned to receive a press fit fastener.

13. A bone fixation system according to claim 9, wherein said at least one opening is an elongated slot.

14. A bone fixation system according to claim 9, wherein said fastener includes a head portion, said at least one opening dimensioned to receive at least a portion of said head portion.

15. A bone fixation system according to claim 14, wherein said head portion is generally spherical, oval, hex or flat.

16. A bone fixation system according to claim 9, wherein said fastener includes a head portion, said head portion having a diameter greater than said at least one opening.

17. A bone fixation system according to claim 1, wherein said plate has a medial side having engagement structure for engaging with at least one of said bone structure.

18. A bone fixation system according to claim 17, wherein said engagement structure includes at least one of: spikes and teeth.

19. A bone fixation system according to claim 1, wherein said plate has a medial side having a surface treatment allowing bone ingrowth.

20. A bone fixation system according to claim 19, wherein said surface treatment includes at least one of: plasma spray, bead sintering, knurling, hydroxyapatite, bioactive material, a plurality of holes, and roughened or otherwise irregular surfaces.

21. A bone fixation system comprising:

an elongated plate means having a top portion, a bottom portion, and a bridge portion integrally spanning between the top portion and bottom portion, said bridge portion for connecting at least two bone structures; and a fastener means for fastening the plate means to said at least two bone structures; and wherein said top and bottom portions each include at least one opening dimensioned to receive said fastener means; and wherein said at least one opening includes a first fastener receiving section having a tapered surface, said fastener means including a mating tapered surface, wherein said mating tapered surface generally matching the tapered surface of said first fastener receiving section; and wherein said fastener means includes a set screw member having a threaded surface; and wherein said at least one opening includes a second fastener receiving section having a mating threaded surface, said mating threaded surface generally matching the threaded surface of said set screw member.

22. A bone fixation system according to claim 21, wherein said set screw member includes an means for aligning said set screw with said at least one opening.

23. A bone fixation system according to claim 21, wherein said fastener means includes a head portion and wherein said at least one opening is dimensioned to receive at least a portion of said head portion.

24. A bone fixation system according to claim 23, wherein said head portion is generally spherical, oval, hex, or flat.

25. A bone fixation system according to claim 21, wherein said fastener means includes a head portion, said head portion having a diameter greater than said at least one opening.

26. A bone fixation system according to claim 21, wherein said at least one opening is an elongated slot.

27. A bone fixation system according to claim 21, wherein said at least one opening includes a section dimensioned to receive a press fit fastener.

28. A bone fixation system comprising:

a three-dimensionally contoured elongated plate having a top portion, a bottom portion, and a bridge portion integrally spanning between said top portion and said bottom portion, said top portion having a medial side comprising three dimensional surface contours extending substantially from an upper end of said top portion to said bridge portion and extending substantially from an anterior side of said top portion to a posterior side of said top portion, and said bottom portion having a medial side comprising three dimensional surface contours extending substantially from a lower end of said bottom portion to said bridge portion and extending substantially from an anterior side of said bottom portion to a posterior side of said bottom portion, said medial side of said top and bottom portions being contoured to anatomically fit both an anterior and a lateral profile of a bone structure;

at least one support structure capable of engaging external surfaces of bone structures at terminal ends of said bone structures; and a fastener for fastening said plate to said bone structures.

29. A bone fixation system according to claim 28, wherein said bridge portion includes at least one window extending from a lateral side through a medial side of said bridge portion for observation of a graft area.

30. A bone fixation stem according to claim 28, wherein said at least one support structure includes ledge members located adjacent to said top and bottom portions.

31. A bone fixation system according to claim 30, wherein said ledge members are connected together to form an intervertebral cage device.

32. A bone fixation system according to claim 30, wherein said ledge members include at least one of: bioresorbable compound, bone graft, or bone graft substitute material.

33. A bone fixation system comprising:

a three-dimensionally contoured elongated plate having a top portion, a bottom portion, and a bridge portion integrally spanning between said top portion and said bottom portion along the longitudinal axis of said three-dimensionally contoured elongated plate, said three-dimensionally contoured elongated plate further having a lateral-medial axis and an anterior-posterior axis, said top portion having a medial side comprising three dimensional surface contours extending substantially from an upper end of said top portion to said bridge portion and extending substantially from an anterior side of said top portion to a posterior side of said top portion wherein said three dimensional surface contours further comprise contours about said longitudinal and said anterior-posterior axes, and said bottom portion having a medial side comprising three dimensional surface contours extending substantially from a lower end of said bottom portion to said bridge portion and extending substantially from an anterior side of said bottom portion to a posterior side of said bottom portion wherein said three dimensional surface contours further comprise contours about said longitudinal and said anterior-posterior axes, said three-dimensional surface contours of said top portion and bottom portion being contoured to anatomically fit both an anterior and a lateral profile of a bone structure;

at least one support structure having medial surface contours extending substantially from an anterior surface of said three-dimensionally contoured elongated plate to a posterior surface of said three-dimensionally contoured elongated plate, said medial surface contours capable of engaging external surfaces of bone structures; and a fastener for fastening said plate to said bone structures.

* * * * *